(12) United States Patent
Miyano

(10) Patent No.: US 7,860,675 B2
(45) Date of Patent: Dec. 28, 2010

(54) PATTERN INSPECTION APPARATUS, PATTERN INSPECTION METHOD, AND PATTERN INSPECTION PROGRAM

(75) Inventor: Hiroyoshi Miyano, Tokyo (JP)

(73) Assignee: NEC Corporation, Tokyo (JP)

( * ) Notice: Subject to any disclaimer, the term of this patent is extended or adjusted under 35 U.S.C. 154(b) by 599 days.

(21) Appl. No.: 11/718,548

(22) PCT Filed: Nov. 4, 2005

(86) PCT No.: PCT/JP2005/020282

§ 371 (c)(1),
(2), (4) Date: Nov. 5, 2007

(87) PCT Pub. No.: WO2006/049243

PCT Pub. Date: May 11, 2006

(65) Prior Publication Data

US 2008/0162061 A1    Jul. 3, 2008

(30) Foreign Application Priority Data

Nov. 5, 2004  (JP) .............................. 2004-322200

(51) Int. Cl.
*G01R 13/00*  (2006.01)

(52) U.S. Cl. ............................ 702/70; 702/81; 382/144
(58) Field of Classification Search .................. 702/81, 702/83, 117, 118, 159, 172; 382/195, 144, 382/149, 150; 250/208.1
See application file for complete search history.

(56) References Cited

U.S. PATENT DOCUMENTS 6,239,909 B1 * 5/2001 Hayashi et al. ............. 359/569
6,289,113 B1 * 9/2001 McHugh et al. ............. 382/117

FOREIGN PATENT DOCUMENTS

| JP | 7-220995 A | | 8/1995 |
|---|---|---|---|
| JP | 8-247738 A | | 9/1996 |
| JP | 08247738 A | * | 9/1996 |
| JP | 10-325806 A | | 12/1998 |
| JP | 11-211671 A | | 8/1999 |
| JP | 11-304453 A | | 11/1999 |
| JP | 2001-264263 A | | 9/2001 |
| JP | 2002-107309 A | | 4/2002 |

OTHER PUBLICATIONS

Machine translation of JP 08247738 A.*

(Continued)

*Primary Examiner*—Manuel L Barbee
(74) *Attorney, Agent, or Firm*—Dickstein Shapiro LLP

(57) ABSTRACT

The present invention has an object of realizing a defect inspection estimated at high accuracy by preparing a reference image that reflects the change of the blur with time from a sampled image and design data. The present invention comprises a point spread function estimating section 23 for estimating a point spread function from an observation image and design information, a convolution image generating section 31 for generating a convolution image by convoluting the point spread function relative to the design information and a reference image generating section 33 for generating a reference image from the convolution image obtained by the convolution image generating section. binary image relative to "chromium on quartz glass".

19 Claims, 16 Drawing Sheets

OTHER PUBLICATIONS

Salik, B. et al.; "Average coherence approximation for partially coherent optical systems"; Journal of the Optical Society of America A, vol. 13, No. 10/Oct. 1996, pp. 2086-2090.

Yatagai, T.; "Physics of Contemporaries 5: Light and Fourier Transform"; Asakura Shoten, 1992, pp. 92-97.

Higashiki, T.; "Optical Lithography Technology-Practical Bases and Problems"; ED Research, Focus Report Series, 2002, pp. 45-49.

Hiyoshi, H.; "Expansion of Gravity Center Coordinates Using Voronoi Diagram and Application Thereof to Multi-Dimensional Data Interpolation"; Applied Mathematics, 2002, pp. 176-190.

Duda, Richard, O., et al.; "Pattern Classification (2nd ed.)", translated by Morio Onoe, 2003, pp. 111-113.

Press, W.H. et al.; "Numerical Recipes", translated by Katsuichi Tankei, Haruhiko Okumura, Toshiro Sato, Makoto Kobayashi, Gijutsu-Hyoron Co., Ltd., published on Nov. 1, 2001, pp. 307.312.

* cited by examiner

FIG.8
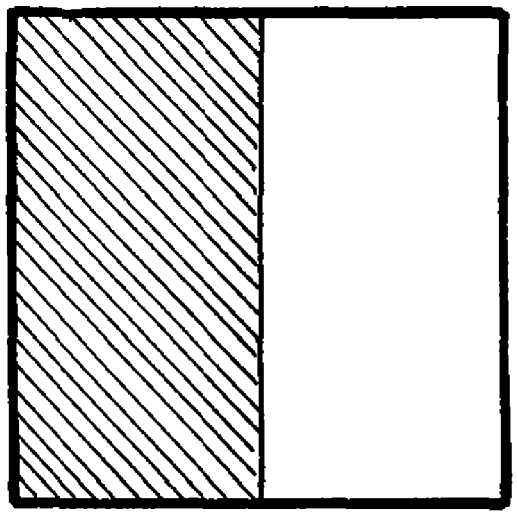
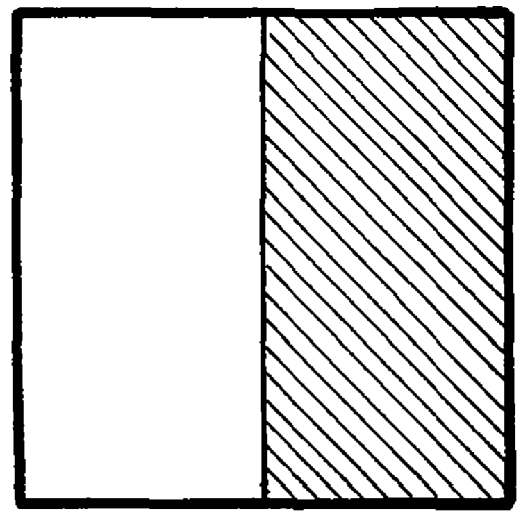
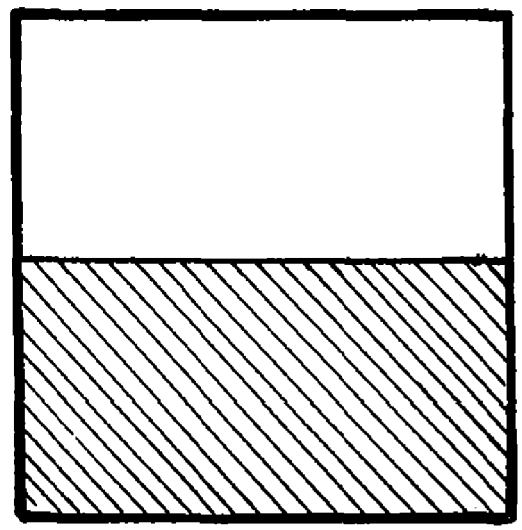
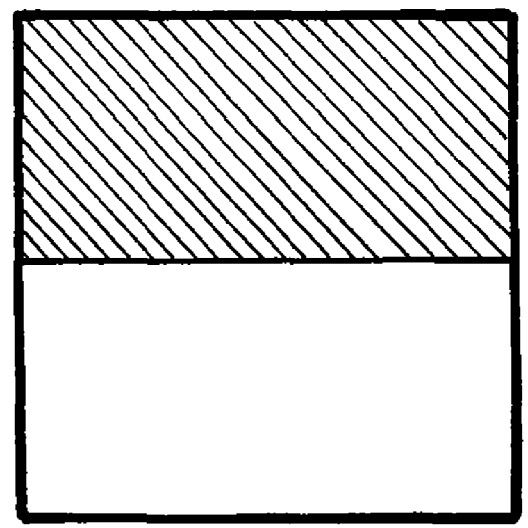

FIG.14
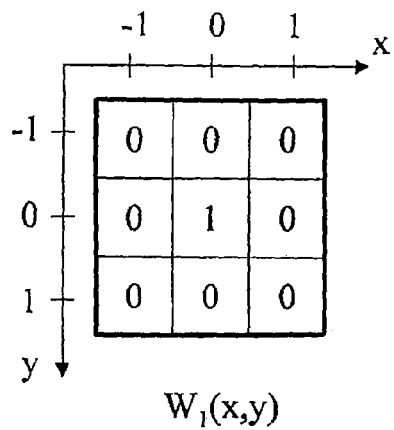
$W_1(x,y)$
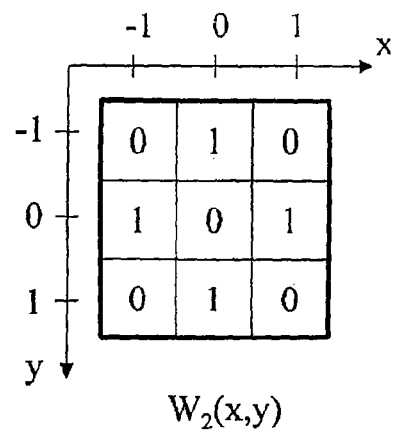
$W_2(x,y)$
FIG.15
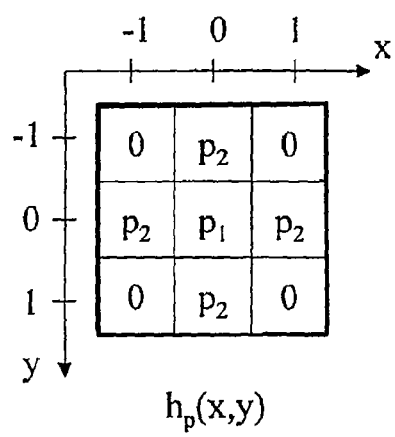
$h_p(x,y)$
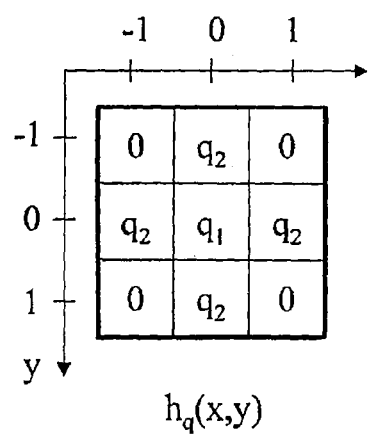
$h_q(x,y)$
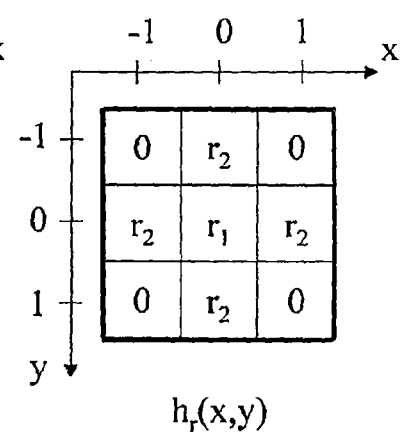
$h_r(x,y)$ R(x,y)

$f_1(x,y)$ $f_2(x,y)$ $R(x,y)$

PATTERN INSPECTION APPARATUS, PATTERN INSPECTION METHOD, AND PATTERN INSPECTION PROGRAM

TECHNICAL FIELD

This invention relates to a pattern inspection apparatus, a pattern inspection method and a pattern inspection program for inspecting a pattern or the like to be used for manufacturing semiconductor integrated circuits. More particularly, the present invention relates to a pattern inspection apparatus, a pattern inspection method and a pattern inspection program that can effectively operate with the change of optical system with time.

BACKGROUND ART

Pattern inspections for checking masks such as reticles and other photo-masks to be used for manufacturing semiconductor integrated circuits are required to be ever more rigorous to respond to the demand for micronized patterns in recent years.

Generally, pattern inspections involve preparing a real image by irradiating the mask to be used with a laser beam or a charged particle beam, also preparing a reference image by computations, using design data of corresponding areas, and comparing the real image and the reference image to find out discrepancies, if any.

To realize a highly accurate defect inspection, it is necessary that the pattern on the real image and the pattern on the corresponding reference image accurately agree with each other for defect-free areas.

Then, the blur of the image, if any, that is produced when the mask prepared by using design data is observed by way of an optical system has to be reproduced by simulation.

A complex transmittance image produced by a mask is defined as E(x, y) for the following description.

The image intensity distribution obtained by way of an optical system is defined as I(x, y) for simulation.

The optical system may be a coherent coupling system or an incoherent coupling system. The impulse response may be defined as K(x, y) and a convolutional operation may be expressed by * as described, for instance, in Non-Patent Document 1.

Then, the image intensity distribution I(x, y) is expressed by formula (1) below for a coherent coupling system,

[formula 1]

$$I(x, y) = |E * K|^2 \quad (1)$$

and by formula (2) below for an incoherent coupling system,

[formula 2]

$$I(x, y) = |E|^2 * |K|^2 \quad (2)$$

so that it can be determined by a convolutional operation in either case.

The impulse response K is a quantity that can be determined from the pupil function and the wave front aberration of the lens.

As described in Non-Patent Document 2, for instance, the image intensity distribution in a partially coherent coupling system is expressed from the Hopkins theory

[formula 3]

$$I(x, y) = \int\int\int\int E(x', y')E^*(\tilde{x}, \tilde{y})J(x' - \tilde{x}, y' - \tilde{y})$$
$$K(x - x', y - y')K^*(x - \tilde{x}, y - \tilde{y})dx'dy'd\tilde{x}d\tilde{y},$$

where J is a function that is referred to as mutual intensity function and can be determined from the pupil function of the objective lens and the condenser lens. J=1 in the case of coherent image formation, whereas J=δ(x, y), which is the Derac's delta function, in the case of incoherent image formation.

For example, Patent Document 1 describes a method of computationally determining the image intensity distribution by using Hopkins theory or the M. Yeung's method, which is a practical application of Hopkins theory, for a complex transmittance image showing a mask.

However, Hopkins theory and M. Yeung's method involve computational operations to a large extent and are hence not easy. In other words, they are not suitable for defect inspection apparatus that are required to check defects in a realistic period of time.

Thus, there are attempts to approximate the operation of Hopkins theory by a convolutional operation.

For example, Non-Patent Document 2 describes a technique as summarily shown below.

If the impulse response computationally determined from the pupil function and the wave front aberration is K and p and f are defined respectively by formulas 4 and 5 below,

[formula 4] (3)

$$\mu(\tilde{x}, \tilde{y}) = \frac{J(\tilde{x}, \tilde{y})}{H(0, 0)}$$

and

[formula 5] (4)

$$f(x - x', y - y') = \frac{\int\int |K(x - x' - \tilde{x}, y - y' - \tilde{y})|^2 \mu(\tilde{x}, \tilde{y}) d\tilde{x}d\tilde{y}}{\int\int |K(x - x' - \tilde{x}, y - y' - \tilde{y})|^2 d\tilde{x}d\tilde{y}},$$

the two point spread functions $K_c$ and $K_i$ are computed in a manner as shown below

[formula 6]

$$K_c = f^{1/2} K$$

$$K_i = (1-f)^{1/2} K$$

and the image intensity distribution is computationally determined by the formula shown below,

[formula 7]

$$I(x, y) = |E * K_c|^2 + |E|^2 * |K_i|^2 \quad (5)$$

by using $K_c$ and $K_i$.

Since J=1 in the case of a coherent image formation system, μ=1 is obtained by using it as substitute in the formula (3). Then, f=1 is obtained by using the latter as substitute in the formula (4). Thus, ultimately the formula (5) agrees with the formula (1). On the other hand, since J=δ(x, y) in the case of an incoherent image formation system, μ=0 is obtained by using it as substitute in the formula (3). Then, f=0 is obtained by using the latter as substitute in the formula (4). Thus, ultimately the formula (5) agrees with the formula (2). In short, the formula (5) can be seen as an approximating expression of a coherent image formation system and a partially coherent image formation system formed by expanding an incoherent image formation system.

Patent Document 2 shows another technique of approximating a partially coherent image formation system with which point spread functions P and Q are computed by using the impulse response K that is also computationally determined from the pupil function and the wave front aberration in a manner as expressed by the formula shown below.

[formula 8]

$$P(x, y) = J(0, 0)|K(x, y)|^2$$
$$Q(x, y) = \begin{cases} 0 & (x, y) = (0, 0) \\ 2K^*(0, 0) \cdot J(x, y) \cdot K(x, y) & \text{otherwise} \end{cases}$$

Then, the image intensity distribution is computationally determined by using P and Q in a manner as expressed by the formula shown below.

[formula 9]

$$I(x, y) = P(x, y)*|E(x, y)|^2 + Re[E^*(x, y)\{Q(x, y)*E(x, y)\}]$$

However, the partially coherent image formation models shown above do not take optical system errors into consideration.

As described in the Non-Patent Document 3, more complex models such as vector image formation models are being discussed because various optical system errors that cannot be reproduced by a partially coherent model are found.

Patent Document 1: JP-07-220995-A

Patent Document 2: JP-2002-107309-A

Patent Document 3: JP-11-304453-A

Patent Document 4: JP-10-325806-A

Patent Document 5: JP-11-211671-A

Non-Patent Document 1: Tyohiko Yatagai, "Physics of Contemporaries 5: Light and Fourier Transform", Asakura Shoten, 1992, pp. 92-97.

Non Patent Document 2: Boaz Salik et al., "Average Coherence Approximation for Partially Coherent Optical Systems", Journal of the Optical Society of America A, 1996, Vol. 13, No. 10, pp. 2086-2090.

Non-Patent Document 3: Tatsuhiko Higashiki, "Optical Lithography Technology—Practical Bases and Problems", ED Research, Focus Report Series, 2002, pp. 45-49.

Non-Patent Document 4: Hisamoto Hiyoshi, "Expansion of Gravity Center Coordinates Using Voronoi Diagram and Application Thereof to Multi-Dimensional Data Interpolation", Applied Mathematics, 2002, pp. 176-190.

Non-Patent Document 5: Richard O. Duda et al., "Pattern Classification (2nd ed.)", translated by Morio Onoe, 2003, pp. 111-113.

Non-Patent Document 6: W. H. Press, P. Flannery, S. A. Teukolsky, W. T. Vetterling, "Numerical Recipes", translated by Katsuichi Tankei, Haruhiko Okumura, Toshiro Sato, Makoto Kobayashi, Gijutsu-Hyoron Co., Ltd, published on Nov. 1, 2001, pp. 307-312.

DISCLOSURE OF THE INVENTION

Problems to be Solved by the Invention

The problem of the conventional art lies in that it cannot raise the precision level of the reference image because it considers only the errors produced due to optical factors that are not considered for models and not the errors that take place due to the change of the optical system with time.

It is true that a simulation model becomes complex when efforts are paid to reduce the errors that arise due to optical factors that are not considered for the model.

However, the parameters used for a simulation model are quantities that accompany changes with time. Therefore the precision level is not raised unless they are observed each time when the mask is checked.

For example, with the model cited above for the conventional art requires the aberration to be observed. However, the aberration can fluctuate to an unnegligible extent due to changes of the temperature, the atmospheric pressure and the accumulated heat of the optical system. Therefore, the precision level of the defect inspection is not raised unless the aberration is observed each time when the mask is checked.

On the other hand, observation of aberration requires the use of a specific optical system and is a very time consuming operation.

Additionally, as the model becomes complex, more parameters needs to be checked for changes with time and it is also very time consuming to observe the increased number of parameters each time when the mask is checked. Such an operation is not practically feasible and cannot be conducted when finding out defects.

Therefore, it is an object of the present invention to make it possible to quickly check errors that arise due to changes with time, while minimizing errors due to optical factors that are not considered for the model.

Means for Solving the Problem

With a defect check system according to the present invention, a reference image is generated by means of a reference image generation method that is based on a convolutional operation using a plurality of point spread functions that can be prepared from a few number of parameters and physically backed so as to include a coherent image formation model and an incoherent image formation model. The few number of parameters for preparing the point spread functions are computationally determined by learning from a real image and part of a design image. As a few number of parameters are used, it is possible to estimate the parameters from the images, bypassing the problem of overlearning. With such an arrangement, it is now possible to reduce errors due to changes with time and also discrepancies from the actual environment in order to improve the precision level of the reference image and achieve the object of the present invention.

In a first aspect of the present invention, there is provided a reference image generation apparatus characterized by comprising: a point spread function estimating section for estimating a point spread function from an observation image and design information; a convolution image generating section for generating a convolution image by convoluting the point spread function relative to the design information; and a reference image generating section for generating a reference image from the convolution image obtained by the convolution image generating section.

Preferably, in the reference image generation apparatus as defined above, the point spread function is plural in number.

Preferably, in the reference image generation apparatus as defined above, the point spread function is expressed by not more than a predetermined number of parameters.

Preferably, in the reference image generation apparatus as defined above, the point spread function is expressed by a Gaussian function.

Preferably, in the reference image generation apparatus as defined above, the point spread function is expressed by a product-sum operation.

Preferably, in the reference image generation apparatus as defined above, the point spread function is isotropic.

Preferably, in the reference image generation apparatus as defined above, the point spread function shows a profile admitting distortions.

Preferably, in the reference image generation apparatus as defined above, the point spread function is expressed by point spread function structuring parameters and point spread expressing parameters and the point spread function estimating section further inputs the point spread function structuring parameters to estimate the point spread function expressing parameters.

Preferably, in the reference image generation apparatus as defined above, the reference image generating section generates the reference image by consolidating a plurality of convolution images according to a partially coherent coupling model.

Preferably, in the reference image generation apparatus as defined above, the point spread function is expressed by point spread function structuring parameters and point spread expressing parameters and the point spread function estimating section further inputs the point spread function structuring parameters to estimate consolidating parameters for the consolidation.

Preferably, in the reference image generation apparatus as defined above, the reference image generated by the convolution image generating section and the reference image generating section is turned to a virtual real image on the basis of a virtual design image and the function estimating section also uses the virtual design image and the virtual real image as input when estimating the point spread function.

Preferably, in the reference image generation apparatus as defined above, the observation image and the design information include not only those relating to the pattern being currently inspected but also the patterns inspected in the past.

In a second aspect of the present invention, there is provided a pattern inspection apparatus characterized by comprising: a reference image generating apparatus as defined above; and an image comparing section for comparing the observation image and the reference image.

In a third aspect of the present invention, there is provided a pattern inspection apparatus characterized by comprising: a means for generating a reference image from an observation image and design information; and a means for performing a pattern inspection by comparing the observation image and the reference image.

Advantages of the Invention

The first advantage that the present invention provides is that it is possible to generate a reference image with a high precision level.

It is because errors that arise due to changes with time can be absorbed as the point spread function is estimated on the basis of an observation image and design information.

The second advantage that the present invention provides is that it is possible to check defect very quickly.

It is because the present invention adopts a reference image generation system that is based on convolutional operations using one or more than one point spread functions.

BRIEF DESCRIPTION OF THE DRAWINGS

FIG. 8 is a schematic illustration of four edge patterns;

FIG. 14 is a schematic illustration of a specific example of point spread function structuring parameters;

FIG. 15 is a schematic illustration of a specific example of point spread function with use of point spread function structuring parameters from the point spread function expressing parameters;

EXPLANATION OF REFERENCE SYMBOLS

Figure 1:
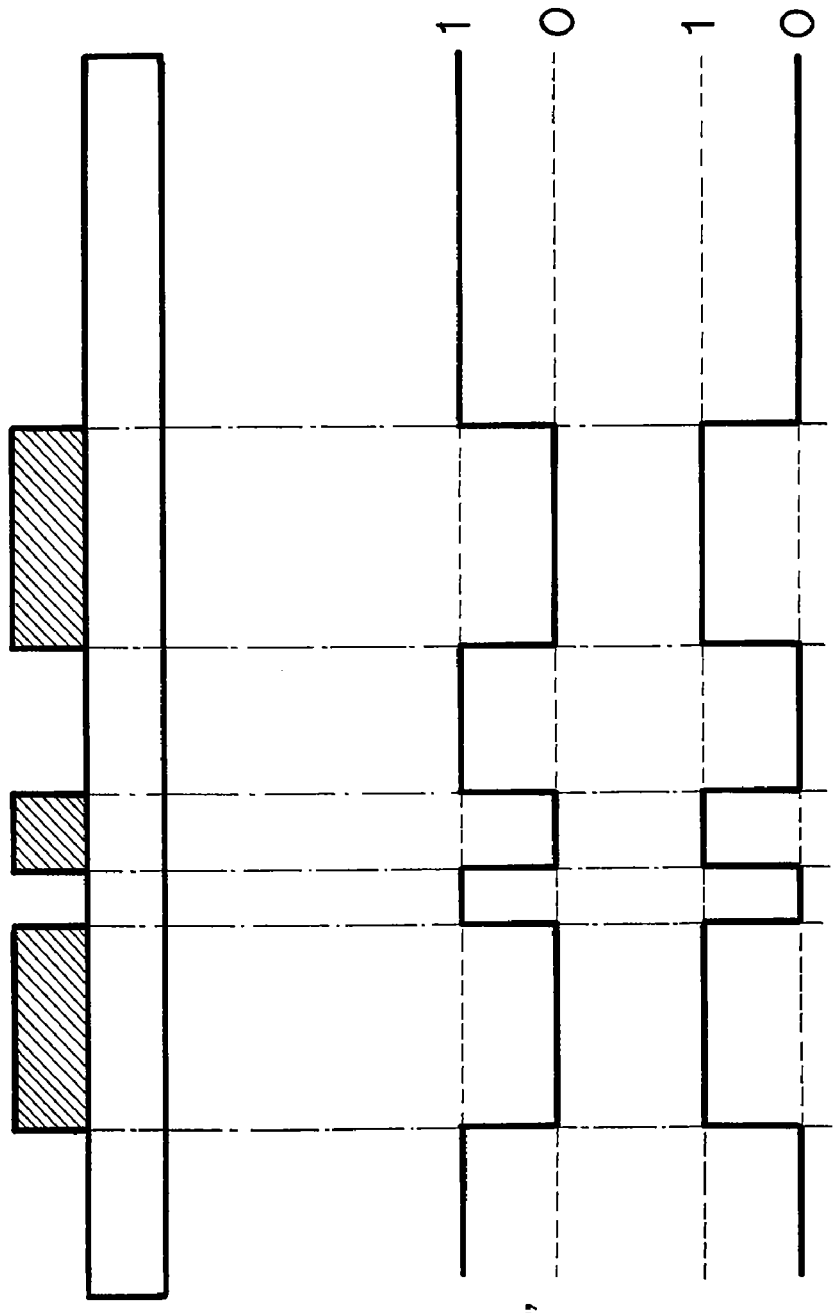
FIG. 1 is a schematic illustration of a binary mask and a corresponding design image.

1: input apparatus
2: data learning apparatus
3: data processing apparatus
4: memory apparatus
5: output apparatus
6: data learning apparatus
7: memory apparatus
8: parameter learning program
9: defect check program
11: real image input means
12: design image input means 21: partial real image extraction means 22: partial design image extraction means 23: point spread function expressing parameter computation means 24: virtual learning image generation means 31: plurality of convoluted images generation means 32: reference image generation means 33: image comparison means Best Mode For Carrying Out The Invention Now, the present invention will be described in greater detail by referring to the accompanying drawings that illustrate the best modes for carrying out the present invention.

Figure 4:
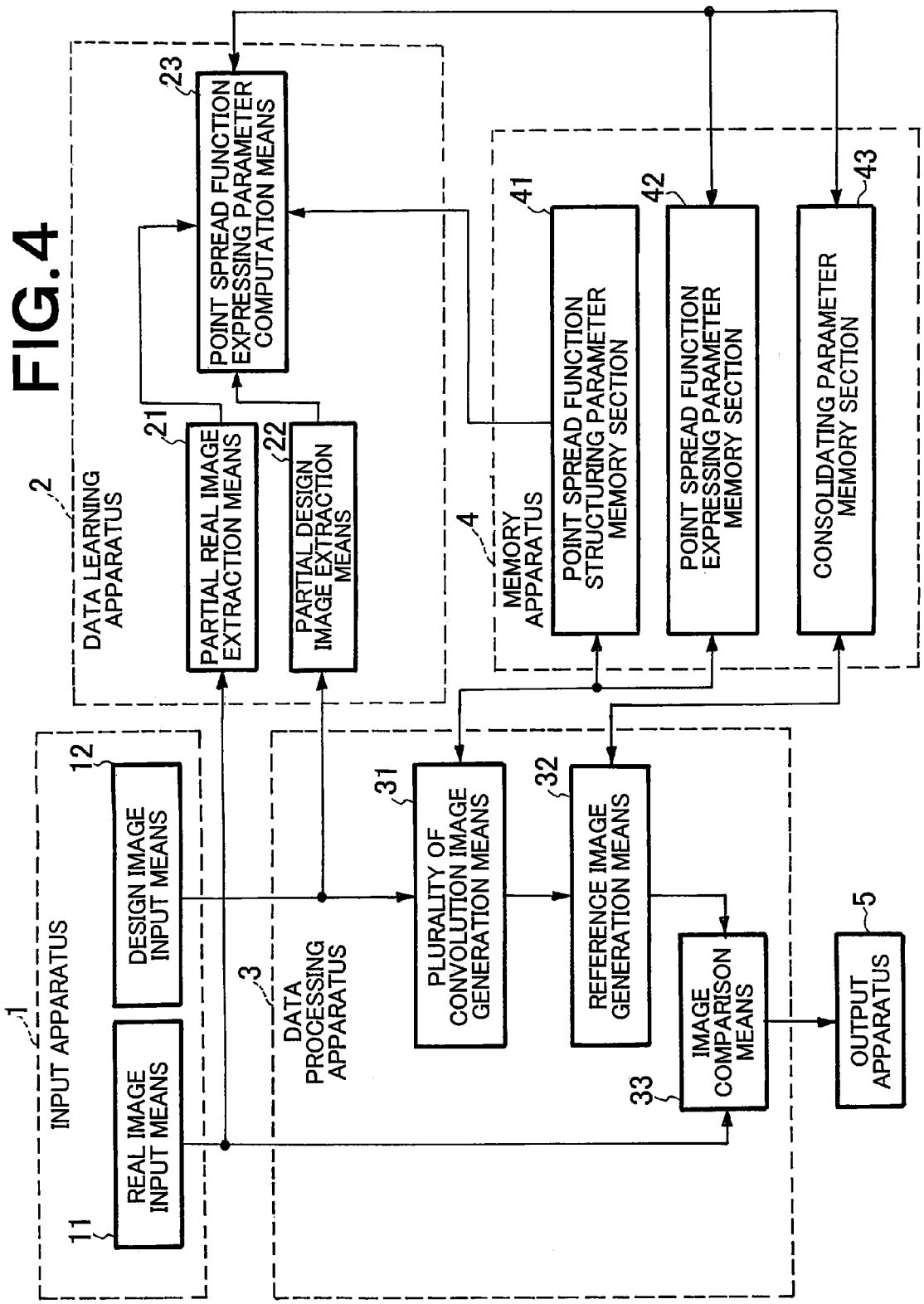
FIG. 4 is a schematic block diagram of an embodiment of the present invention in the first aspect thereof.

With reference to FIG. 4, the first embodiment of the present invention includes an input apparatus 1 for inputting an image, a data learning apparatus 2 adapted to operate under the control of a program, a data processing apparatus 3 adapted to operate under the control of a program, a memory apparatus 4 for storing information and an output apparatus 5 which may include a display apparatus and/or a printing apparatus.

The input apparatus 1 includes a real image input means 11 and a design image input means 12.

The real image input means 11 images the mask to be inspected for defects as real image by scanning the mask with a laser beam or a charged particle beam and converting the detected quantity of light into an electric signal. The image taken in by the real image input means 11 is defined as R(x, y). The real image input means 11 is not limited to a transmission optical system and a reflection optical system may alternatively be adopted to acquire a real image without any problem.

The design image input means 12 inputs the design data of the mask to be inspected for defects.

Here, the method of expressing an image of a mask by means of design data will be described below. The image is expressed by means of two coordinates including an x-coordinate and a y-coordinate.

Since a mask is formed by using a plurality of materials, the design data of the mask can be expressed as a set of binary images, each indicating the presence or absence of each of the materials.

For example, if the mask is a chromium mask having a chromium shield section formed on a quartz glass, it can be expressed by binary images, each of which takes the value of 1 when the region thereof has only quartz glass and 0 when the region thereof has not only quartz glass but also chromium, and binary images, each of which takes the value of 1 when the region has chromium and 0 when the region does not have chromium.

Figure 2:
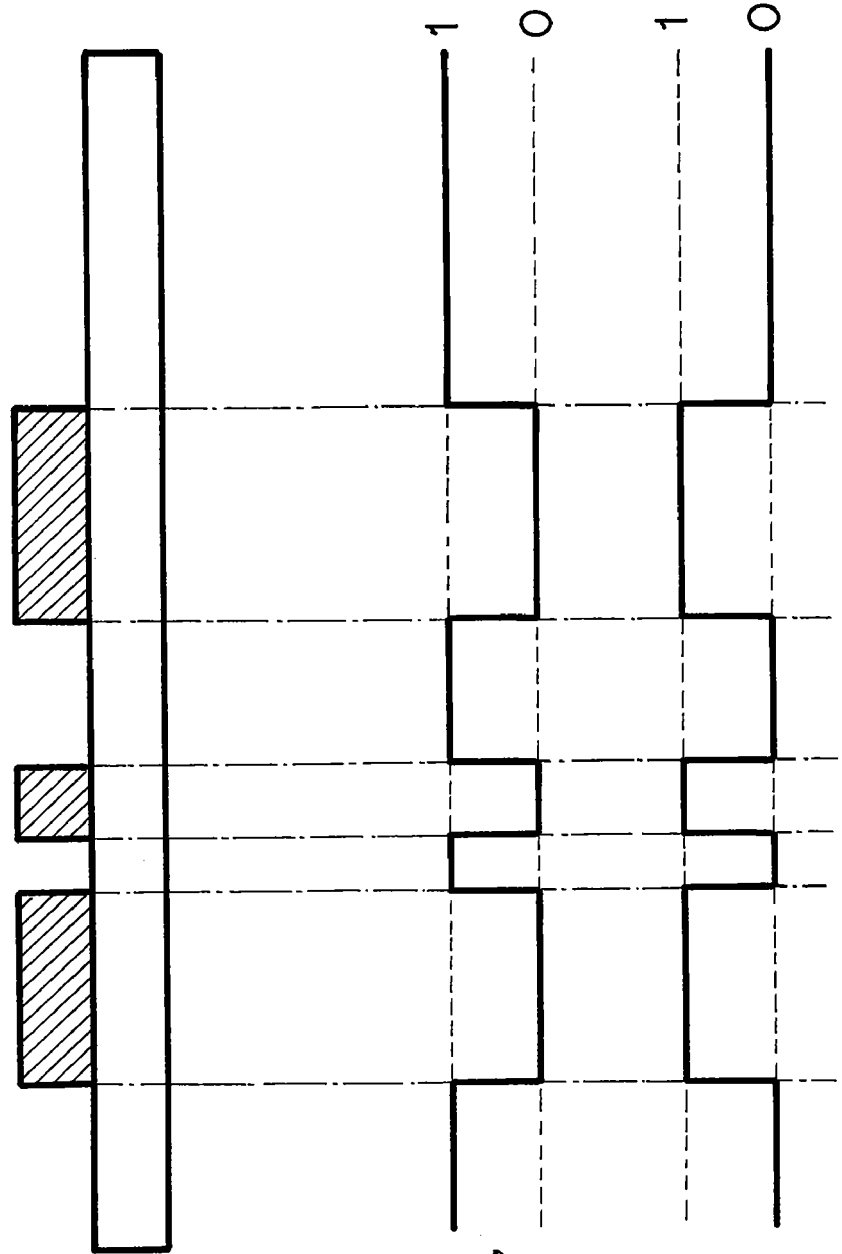
FIG. 2 is a schematic illustration of a half tone mask and a corresponding design image.

Referring now to FIG. 2, if the mask is a phase shift mask where one or more than absorbents are arranged, it can be expressed by binary images, each of which takes a value that represents a region having quartz glass or another value that represents a region where an absorbent is found.

Figure 3:
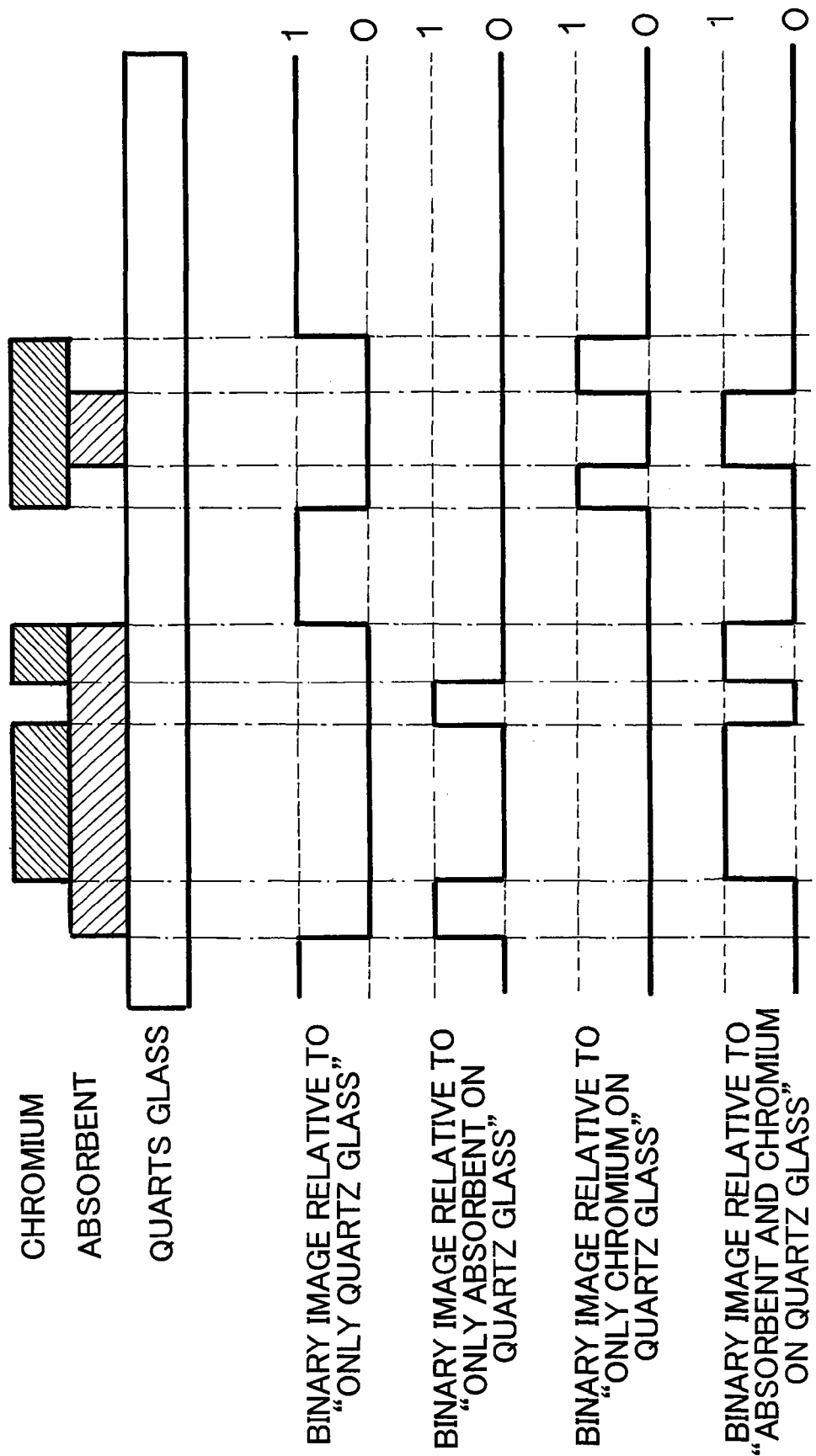
FIG. 3 is a schematic illustration of a tri-tone mask and a corresponding design image.

Referring now to FIG. 3, if the mask is a tri-tone mask formed by using quartz glass, one or more than one absorbents and chromium, it can be expressed by binary images of four different types because there can be regions where only quartz glass is found, those where only an absorbent is arranged on quartz glass, those where only chromium is arranged on quartz glass and those where both an absorbent and chromium are arranged on quartz glass.

If the number of binary images for expressing a mask is M, the M binary images is defined as $f_m(x, y)(m=1, \ldots, M)$, The transmittances of the M different materials are defined as $a_1, \ldots, a_M$.

Since at least one of the M materials should be found on any of the regions on the mask, the relationship expressed by the formula below holds true.

[formula 10] (6)

$$\sum_{m=1}^{M} f_m(x, y) = 1$$

As described in the Patent Documents 2 and 3, the binary images of an image showing design data can be expanded to multiple-valued images in order to express binary images having a resolution higher than that of the corresponding image.

For the design image $f_m(x, y)$, an image that has been subjected to a process of absorbing manufacturing errors by rounding the corners of the pattern at the time of preparing the mask as described in the Patent Document 3 may be used instead of an image of the design information of a simple mask as shown in FIG. 1 or 2.

Now, the conventional method of preparing a reference image, or the conventional simulation method will be described below.

A simulation starts on an assumption that the mask is an image showing a complex transmittance. The transmittance E(x, y) of the mask is expressed by the formula shown below.

[formula 11]

$$E(x, y) = \sum_{m=1}^{M} a_m f_m(x, y)$$

Additionally, the absolute value of the transmittance of the mask |E(x, y)| is expressed by the formula below.

[formula 12]

$$|E(x, y)| = \sum_{m=1}^{M} a_m \left| f_m(x, y) \right|$$

The memory apparatus 4 includes a point spread function structuring parameter memory section 41, a point spread function expressing parameter memory section 42 and a consolidating parameter memory section 43.

The point spread function parameter structuring memory section 41 stores the parameters that are required when structuring a point spread function from the parameters stored in the point spread function expressing parameter memory section 42. In the following, the parameters stored in the point spread function parameter structuring parameter memory section 41 are referred to as point spread structuring parameters.

The point spread function expressing parameter memory section 42 stores parameter sets of three different types that are used to express three point spread functions. In the following, the parameter sets of the three different types are defined respectively as p, q and r and the parameters p, q and r are referred to as point spread function expressing parameters respectively. Each of the parameter sets p, q and r includes one or more than one parameters.

It is possible to prepare three point spread functions from the parameter sets p, q and r of the three types stored in the point spread function expressing parameter memory section 42, using the parameters stored in the point spread function structuring parameter memory section 41. For the following description, the point spread function structured from the point spread function expressing parameter p, the point spread function structured from the point spread function expressing parameter q and the point spread function structured from the point spread function expressing parameter r are defined respectively as $h_p(x, y)$, $h_q(x, y)$ and $h_r(x, y)$.

Now, assume here that a point spread function can be expressed as the sum of two isotropic two-dimensional normal distributions as an example for the point spread function expressing parameters and the point spread function structuring parameters.

An isotropic two-dimensional normal distribution refers to a function expressed by $$GAUSS(\mu, v, \sigma) = (1/(2\Pi\sigma^2))\exp[-((x-\mu)^2 + (y-v)^2)/2\sigma^2]].$$

Then, data as shown below may typically be stored in the point spread function expressing parameter memory section 42 and the point spread function structuring parameter memory section 41.

$p=(\sigma_1, \sigma_1')$ $q=(\sigma_2, \sigma_2')$ and $r=(\sigma_3, \sigma_3')$ are stored as point spread function expressing parameters.

$\mu, \mu', v, v'$ and t are stored as point spread function structuring parameters.

Thus, from the point spread function expressing parameters and the point spread function structuring parameters listed above, the point spread function is expressed as the sum of two isotropic normal distributions shown below.

$$h_p(x, y) = (1-t) \cdot GAUSS(\mu, v, \sigma_1) + t \cdot GAUSS(\mu', v', \sigma_1')$$
$$h_q(x, y) = (1-t) \cdot GAUSS(\mu, v, \sigma_2) + t \cdot GAUSS(\mu', v', \sigma_2')$$
$$h_r(x, y) = (1-t) \cdot GAUSS(\mu, v, \sigma_3) + t \cdot GAUSS(\mu', v', \sigma_3')$$

It is also possible to change the way of sorting point spread function structuring parameters and point spread function expressing parameters when structuring a point spread function as the sum of two isotropic two-dimensional normal distributions. For example, it may alternatively be so arranged that $p=(\sigma_1, \sigma_1', t_1)$ $q=(\sigma_2, \sigma_2', t_2)$ and $r=(\sigma_3, \sigma_3', t_3)$ are stored as point spread function expressing parameters and $\mu, \mu', v$ and $v'$ are stored as point spread function structuring parameters.

From the point spread function expressing parameters and the point spread function structuring parameters listed above, the point spread function may be expressed as the sum of two isotropic normal distributions shown below.

$$h_p(x, y) = (1-t_1) \cdot GAUSS(\mu, v, \sigma_1) + t_1 \cdot GAUSS(\mu', v', \sigma_1')h_q(x, y)$$
$$= (1-t_2) \cdot GAUSS(\mu, v, \sigma_2) + t_2 \cdot GAUSS(\mu', v', \sigma_2')h_r(x, y)$$
$$= (1-t_3) \cdot GAUSS(\mu, v, \sigma_3) + t_3 \cdot GAUSS(\mu', v', \sigma_3')$$

It is also possible to express a point spread function as the sum of more than two two-dimensional normal distributions instead of the sum of two two-dimensional normal distributions.

Still alternatively, it is also possible to assume non-isotropic two-dimensional normal distributions.

As another example, it is also conceivable to structure a point spread function by means of product-sum operations. Then, $p=(p_1, \ldots, p_z)$ $q=(q_1, \ldots, 1_z)$ and $r=(r_1, \ldots, r_z)$ are stored as point spread function expressing parameters.

Z function values $w_z(x, y)(z=1, \ldots, Z)$ are stored as point spread function structuring parameters.

From the point spread function expressing parameters and the point spread function structuring parameters as listed above, a point spread function can be structured by means of product-sum operations as shown below.

$h_p(x, y) = \Sigma_z p_z w_z(x, y)$, $h_q(x, y) = \Sigma_z q_z w_z(x, y)$ and $h_r(x, y) = \Sigma_z r_z w_z(x, y)$ Any of various methods may be used to specifically define point spread function structuring parameters $w_z(x, y)$ $(z=1, \ldots, Z)$.

For example, a point spread function may be expressed by interpolation.

Figure 6:
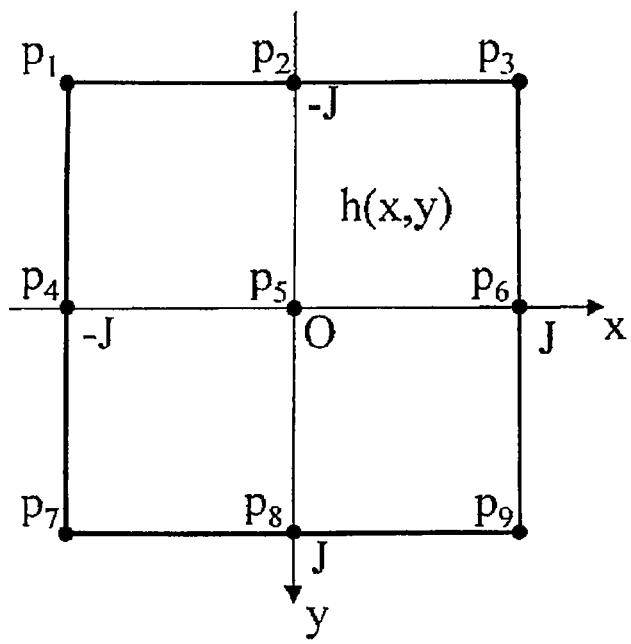
FIG. 6 is a schematic exemplary illustration of determining a point spread function from a rectangle by interpolation.

As an example, assume that a point spread function is a function defined by the integer value of $x=-J, \ldots, +J$, $y=-J, \ldots, +J$ and that the point spread function is structured by segment linear interpolation, using the values $h_1$ through $h_9$ at nine points as shown in FIG. 6.

$p_1=(-J, -J)$, $p_2=(0, -J)$, $p_3=(+J, -J)$, $p_4=(-J, 0)$, $p_5=(0, 0)$, $p_6=(+J, 0)$, $p_7=(+J, +J)$, $p_8=(0, +J)$ and $p_9=(+J, +J)$ If $s=|x|/J$ and $t=|y|/J$ are defined, the following expression holds true.

[formula 13]

$$h(x, y) = \begin{cases} (1-s)(1-t)h_5 + s(1-t)h_4 + (1-s)th_2 + sth_1 & (x<0, y<0) \\ (1-s)(1-t)h_5 + s(1-t)h_6 + (1-s)th_2 + sth_3 & (x \geq 0, y<0) \\ (1-s)(1-t)h_5 + s(1-t)h_4 + (1-s)th_8 + sth_7 & (x<0, y \geq 0) \\ (1-s)(1-t)h_5 + s(1-t)h_6 + (1-s)th_8 + sth_9 & (x \geq 0, y \geq 0) \end{cases}$$

When the following equations are defined,

[formula 14]

$$(x, y) = \sum_{z=1}^{9} h_z w_z(x, y)$$

$$w_1(x, y) = \begin{cases} st & (x<0, y<0) \\ 0 & (\text{otherwise}) \end{cases}$$

$$w_2(x, y) = \begin{cases} (1-s)t & (y<0) \\ 0 & (\text{otherwise}) \end{cases}$$

$$w_3(x, y) = \begin{cases} st & (x \geq 0, y<0) \\ 0 & (\text{otherwise}) \end{cases}$$

[formula 15]

$$w_4(x, y) = \begin{cases} s(1-t) & (x<0) \\ 0 & (\text{otherwise}) \end{cases}$$

$$w_5(x, y) = (1-s)(1-t)$$

$$w_6(x, y) = \begin{cases} s(1-t) & (x \geq 0) \\ 0 & (\text{otherwise}) \end{cases}$$

[formula 16]

$$w_7(x, y) = \begin{cases} st & (x<0, y \geq 0) \\ 0 & (\text{otherwise}) \end{cases}$$

$$w_8(x, y) = \begin{cases} (1-s)t & (y \geq 0) \\ 0 & (\text{otherwise}) \end{cases}$$

$$w_9(x, y) = \begin{cases} st & (x \geq 0, y \geq 0) \\ 0 & (\text{otherwise}) \end{cases}$$

then a point spread function can be structured by means of product-sum operations of

[formula 17]

$$h(x, y) = \sum_{z=1}^{9} h_z w_z(x, y)$$

Since a point spread function shows small absolute values at the outskirt thereof, the corner values of $h_1$, $h_3$, $h_7$ and $h_9$ may be fixed to 0 and the point spread function may be structured by using five function values of $w_2$, $w_4$, $w_5$, $w_6$ and $w_8$.

While a point spread function is structured by dividing it by four rectangles and by using linear interpolation, it is possible to divide it more finely to increase the number of rectangle.

The linear interpolation may be replaced by interpolation of a higher order and the interpolation using rectangles may be replaced by interpolation, dividing the point spread function by triangles or by interpolation, using the Voronoi division described in Non-Patent Document 4.

In addition to the above described ones, interpolation methods based on an assumption that a point spread function is isotropic are also conceivable.

For instance, if a point spread function takes the value of $h_1$ at the origin and the Z+1 values of $h_1, h_2, \ldots, h_z$, 0 at points separated from the origin respectively by the distances of $r_1(=0) < r_2 < \ldots, < r_z < r_{z+1}$ and the formulas shown below are defined

[formula 18]

$$r = \sqrt{x^2 + y^2}$$

[formula 19]

$$w_z(x, y) = \begin{cases} 0 & (r \leq r_{z-1}, r > r_{z+1}) \\ \dfrac{r - r_{z-1}}{r_z - r_{z-1}} & (r_{z-1} \leq r < r_z) \\ \dfrac{r_{z+1} - r}{r_{z+1} - r_z} & (r_z \leq r < r_{z+1}) \end{cases}$$

then an isotropic point spread function can be structured by means of product-sum operations shown below.

[formula 20]

$$h(x, y) = \sum_{z=1}^{Z} h_z w_z(x, y)$$

It is also conceivable to expand the above-described interpolation method beyond the complete isotropy so as to allow distortions among directions.

Assume here that there are distortions in the directions of vectors $u_1, \ldots, u_k$. Also assume that the angles that the vectors make with the x-axis are $\theta_1, \ldots, \theta_k$ respectively.

Figure 7:
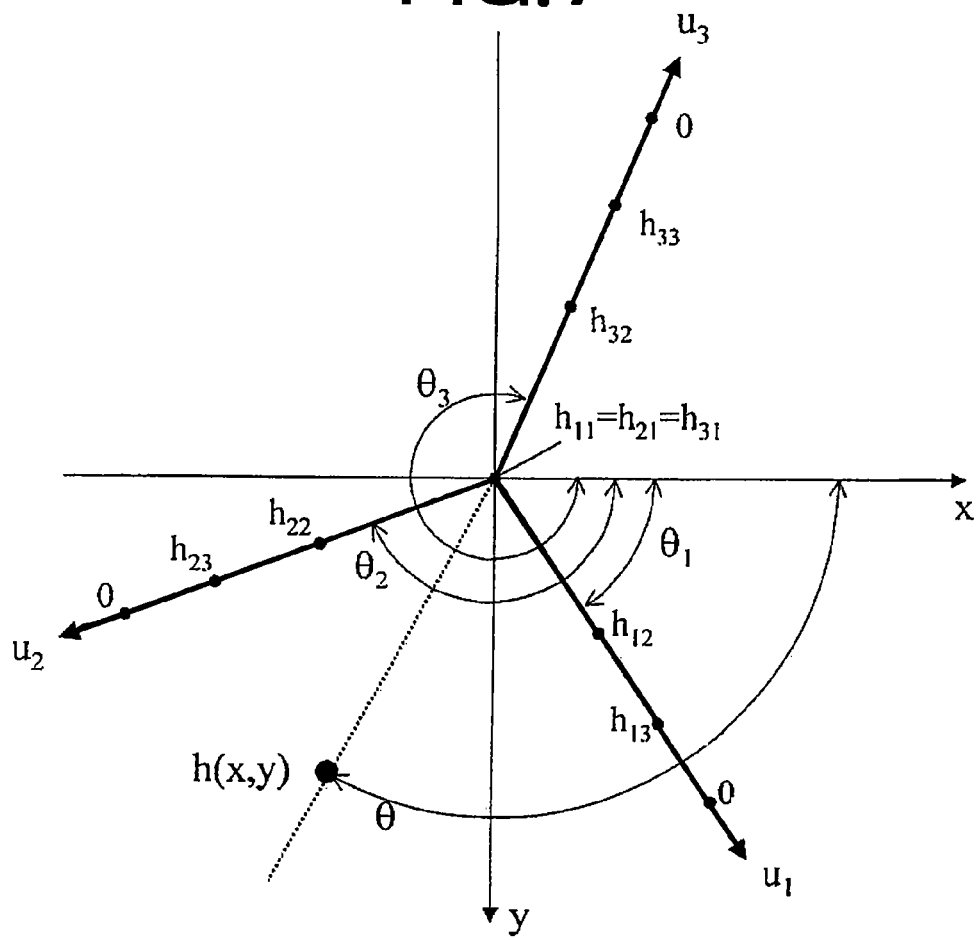
FIG. 7 is another schematic exemplary illustration of determining a point spread function from a rectangle by interpolation.

Additionally assume that the values of a point spread function are $h_{k1}, h_{k2}, \ldots, h_{kz}$, 0 hen the points on the half-line extending from the origin in the direction of the vector $u_k$ are separated from the origin respectively by distances $r_1 (=0) < r_2 \ldots < r_z < r_{z+1}$ ($k=1, \ldots, K$). Now, let us take the vectors $u_1, u_2, u_3$ showing the respective angles $\theta_1, \theta_2, \theta_3$. FIG. 7 shows their values when $Z=3$.

When $\theta$ is the angle between each vector (x, y) and the x-axis and the formula below is defined

[formula 21]

$$w_{\ell,z}(x, y) \begin{cases} \dfrac{\theta - \theta_\ell}{\theta_\ell - \theta_{\ell-1}} \cdot \dfrac{r - r_{z-1}}{r_z - r_{z-1}} & (\theta_{\ell-1} \leq \theta < \theta_\ell, r_{z-1} \leq r < r_z) \\ \dfrac{\theta - \theta_\ell}{\theta_\ell - \theta_{\ell-1}} \cdot \dfrac{r_{z+1} - r}{r_{z+1} - r_z} & (\theta_{\ell-1} \leq \theta < \theta_\ell, r_z \leq r < r_{z+1}) \\ \dfrac{\theta_\ell - \theta}{\theta_{\ell+1} - \theta_\ell} \cdot \dfrac{r - r_{z-1}}{r_z - r_{z-1}} & (\theta_\ell \leq \theta < \theta_{\ell+1}, r_{z-1} \leq r < r_z) \\ \dfrac{\theta_\ell - \theta}{\theta_{\ell+1} - \theta_\ell} \cdot \dfrac{r_{z+1} - r}{r_{z+1} - r_z} & (\theta_\ell \leq \theta < \theta_{\ell+1}, r_z \leq r < r_{z+1}) \\ 0 & (\text{otherwise}), \end{cases}$$

then it is possible to structure a point spread function by means of product-sum operations expressed by the equation shown below.

[formula 22]

$$h(x, y) = \sum_{\ell,z} h_{\ell z} w_{\ell z}(x, y)$$

Apart from the approach using interpolation, it is also possible to structure a point spread function on the basis of principal component analysis if a large amount of information on one or more than one point spread functions estimated in the past is available. For example, if point spread function $h(x, y)$ is a function defined by integers of $x=-J, \ldots, +j$, $y=-J, \ldots, +J$, a point spread function can be expressed by means of $(2J+1)^2$ numerical values so that the above point spread function can be expressed on a point in a $(2J+1)^2$-dimensional space. If the results obtained by estimating a large number of point spread functions are available, the large volume of data may be expressed all as points on the $(2J+1)^2$-dimensional space and the set of points may be subjected to a principal component analysis as described in the Non-Patent Document 5. Then, it is possible to define the z-th principal component as $w_z(x, y)$, using only the first Z-components out of all of the obtained principal components.

All of the various point spread function structuring methods as described above can adjust the number of Z. Therefore, it is only necessary to select an appropriate value for Z, taking the number of data to be learnt into consideration.

The consolidating parameter memory section 43 stores the parameters that are required when computing the pixel values of a reference image from the outcome of the convolutional operations using point spread functions. In the following, the parameters stored in the consolidating parameter memory section 43 are referred to as consolidating parameters.

The data processing apparatus 3 is a defect checking apparatus and includes a plurality of convolution images generation means 31, a reference image generation means 32 and image comparison means 33.

The plurality of convolution images generation means 31 performs a convolutional operation for the three point spread functions $h_p$, $h_q$ and $h_r$ reproduced from the parameters stored in a point spread function parameter reproduction/memory section 42 and the point spread function structuring parameter memory section 41 on the M images $f_1(x, y), \ldots, f_m(x, y)$ supplied from the design image input means 12 to generate 3M images $f_m*h_p(x, y)$, $f_m*h_q(x, y)$ and $f_m*h_r(x, y)$ (where $m=1, \ldots, M$).

The reference image generation means 32 generates consolidates the 3M images obtained by the plurality of convolution images generation means 31, utilizing the parameters obtained from the consolidating parameter memory 25 section 43, to generate a single reference image.

The reference image is an image estimated by means of a computation process from the M design images obtained from the design image input means 12 for the real image obtained by the real image input means 11. Note that the reference images are defined by $G(x, y)$.

$G(x, y)$ can be computed in the following manner by means of the approximate computation technique using the formula (5), using consolidating parameters $C$, $a_m$, $b_m$, $c_m$ ($m=1, \ldots, M$).

[formula 23]

$$G(x, y) = \left[\sum_{m=1}^{M}\{a_m(f_m*h_p) - b_m(f_m*h_q)\}\right]^2 + \left[\sum_{m=1}^{M}\{b_m(f_m*h_p) + a_m(f_m*h_q)\}\right]^2 + \sum_{m=1}^{M}c_m(f_m*h_r) + C \quad (7)$$

The above equation agrees with the formula (5) if $a_m$=Re$[a_m]$, $b_m$=Im$[a_m]$ (where $m=1, \ldots, M$), $h_p$=Re-$[K_c]$, $h_q$=Im$[K_c]$, $h_r$=$K_i$ and $C=0$.

Additionally, if $a_m$=Re$[a_m]$, $b_m$=Im$[a_m]$ (where $m=1, \ldots, M$), $h_p$=Re$[K]$, $h_q$=Im$[K]$, $h_r$=0 and $C=0$, the equation shown below holds true.

[formula 24]

$$G(x, y) = \left|\sum_{m=1}^{M} a_m f_m * K\right|^2 = |E*K|^2$$

Therefore, the formula (7) shows the coherent image expressed by the formula (1).

Now, if $h_p$=0, $h_q$=0, $c_m$=$|a_m|^2$, $h_r$=$|K|^2$ and $C=0$, the equation shown below holds true.

[formula 25]

$$G(x, y) = \sum_{m=1}^{M} |a_m|^2 f_m * |K|^2 = |E|^2 * |K|^2$$

Therefore, the formula (7) shows the coherent image expressed by the formula (2). In short, the formula (7) is a model that includes both a coherent image formation model and an incoherent image formation model and also an approximate partially coherent image formation model.

Light is converted into an electric signal when obtaining an image. One or more than one roots may be involved in the conversion. This is because computations involving squares intervene between energy and an electric current or a voltage with regard to an electric circuit as shown below.

(unit time energy) =(current)$^2$×(resistance)= (voltage)$^2$ × (resistance)$^{-1}$ Therefore, conversely one or more than one roots may be involved when energy is observed by way of an electric current or a voltage.

In view of this problem, the formula (7) may be replaced by the formula shown below when preparing a reference image.

[formula 26]

$$G(x, y) = \sqrt{\left[\sum_{m=1}^{M}\{a_m(f_m*h_p) - b_m(f_m*h_q)\}\right]^2 + \left[\sum_{m=1}^{M}\{b_m(f_m*h_p) + a_m(f_m*h_q)\}\right]^2 + \sum_{m=1}^{M}c_m(f_m*h_r)} + C$$

When this formula is employed, the form of square-sum may be used in the roots in order to assume non-negativity in the roots of G(x, y) as shown by the formula below.

[formula 27]

$$G(x, y) = \sqrt{\left[\sum_{m=1}^{M}\{a_m(f_m * h_p) - b_m(f_m * h_q)\}\right]^2 + \left[\sum_{m=1}^{M}\{b_m(f_m * h_p) + a_m(f_m * h_q)\}\right]^2 + \left[\sum_{m=1}^{M} c_m(f_m * h_r)\right]^2} + C$$

The linear relationship between the input and the output may not be sufficient in the sensor system of an electronic signal conversion section or an observation section to consequently involve logarithm. The formula shown below may be used to cope with such a situation.

[formula 28]

$$G(x, y) = \log\left\{\left[\sum_{m=1}^{M}\{a_m(f_m * h_p) - b_m(f_m * h_q)\}\right]^2 + \left[\sum_{m=1}^{M}\{b_m(f_m * h_p) + a_m(f_m * h_q)\}\right]^2 + \sum_{m=1}^{M} c_m(f_m * h_r)\right\} + C$$

When the relationship of the formula (6) is used, it is possible to eliminate the terms involving fm in order to reduce the quantity of computations. The equation shown below is obtained by eliminating the terms involving fm from the formula (7), using the formula (6).

[formula 29]

$$G(x, y) = \left[V_p - V_q + \sum_{m=1}^{M-1}\{(a_m - a_M)(f_m * h_p) - (b_m - b_M)(f_m * h_q)\}\right]^2 +$$

$$\left[V_p + V_q + \sum_{m=1}^{M-1}\{(b_m - b_M)(f_m * h_p) + (a_m - a_M)(f_m * h_q)\}\right]^2 +$$

$$V_r + \sum_{m=1}^{M-1}(c_m - c_M)(f_m * h_r) + C$$

If the consolidating parameters are A, B, C, $a_m$, $b_m$, $c_m$ (m=1, ..., M), the above formula can be reduced to the formula show belown by replacing the variables as $V_p - V_q \rightarrow A$, $V_p + V_q \rightarrow B$, $V_r + C \rightarrow C$, $a_m - a_M \rightarrow a_m$, $b_m - b_M \rightarrow b_m$, $c_m - c_M \rightarrow c_m$ and $M-1 \rightarrow M$.

[formula 30]

$$G(x, y) = \left[\sum_{m=1}^{M}\{a_m(f_m * h_p) - b_m(f_m * h_q)\} + A\right]^2 + \left[\sum_{m=1}^{M}\{b_m(f_m * h_p) + a_m(f_m * h_q)\} + B\right]^2 + \sum_{m=1}^{M} c_m(f_m * h_r) + C \quad (8)$$

Thus, the reference image can be computationally determined by using the formula (8).

Additionally, any of the various expansion techniques used for the formula (7) may also be applied to the formula (8).

The image comparison means 33 compares the real image R(x, y) obtained by the real image input means 11 and the reference image G(x, y) obtained by the reference image generation means 32 and determines that the real image is defective when the difference between the two images is significant. More specifically, it determines a region where the relationship shown below holds true

[formula 31]

$$|R(x, y) - G(x, y)| > T$$

by using a predetermined constant T.

Any of the techniques described in the Patent Document 4 and the Patent Document 5 may be used to check a defective image.

The technique of the Patent Document 4 has the objective of providing a method and an apparatus that can very quickly and highly accurately carry out an appearance inspection of a micro-pattern. According to the Patent Document 4, inspection image characteristic data are generated by inputting an inspection image of an object and a reference image that corresponds to the inspection image and adding the absolute values of the differences of luminance between each of the pixels of the inspection image and the pixels of the surrounding inspection pixel region formed by nearby pixels and also the absolute values of the differences of luminance between each of the pixels of the reference image and the pixels of the surrounding reference pixel region formed by nearby pixels. Then, the inspection image characteristic data and the reference image characteristic data for each pixel are compared to determine the defect or defects of the object.

The technique of the Patent Document 5 has the objective of providing an appearance inspection method and an appearance inspection apparatus that can detect a foreign object having optical properties same as a detection pattern and reduce the frequency of producing a pseudo defect if the concentration gradient differs at and near an edge so as to consequently reduce the time of necessary computations and the memory region. The appearance inspection apparatus comprises an edge detection means for detecting edges forming an edge element image from an input image, an edge linking means for linking edge elements to generate a single edge, giving the same label to edges having mutual distances found within a reference value, a profile identification means for identifying the coordinates of the position and the type of each foreign object and/or those of each profile defect from the edge elements and outputting them and an image holding means for marking the coordinates of the position of each foreign object and/or that of each profile defect output from the profile identifying means and storing them. The profile identification means 4 is adapted to recognize the position of each foreign object and/or that of each profile defect from the radius of curvature of each edge element, the distance between the edge element and an edge element part running in parallel and the area of the closed region.

The data learning apparatus 2 is an apparatus to be operated to learn the change of the optical system with time before the data processing apparatus is operated to check defects and includes a partial real image extraction means 21, a partial design image extraction means 22 and a point spread function expressing parameter computation means 23.

The partial real image extraction means 21 extracts a partial region to be used for learning from the real image obtained by the real image input means 11. The region to be used for learning is defined as L hereinafter.

The partial design image extraction means 22 extracts a partial region that corresponds to the partial region of the real image extracted by the partial real image extraction means 21 from the design image obtained by the design image input means 21.

The point spread function expressing parameter computation means 23 computationally determines point spread function expressing parameters p, q, r from the partial region of the real image obtained by the partial real image extraction means 21, the partial region of the design image obtained by the partial design image extraction means 22 that corresponds to the partial region of the real image and the point spread function structuring parameters stored in the point spread function structuring parameter memory section 41 and stores the computationally determined point spread function expressing parameters in the point spread function expressing parameter memory section 42 and the computationally determined consolidating parameters in the consolidating parameter memory section 43.

The point spread function expressing parameters p, q, r are computationally determined by determining p, q, r and the consolidating parameters that minimize the error $S_L$ of the reference image and the real image of the partial region as expressed by the formula below

[formula 32]

$$S_L = \Sigma_{(x, y) \in L} |R(x, y) - G(x, y)|^2 \qquad (9)$$

so as to make it possible to reproduce the partial region better from the partial region of the design image to be used for leaning.

An optimization technique that can be used when an objective function is a multi-variable function can also be used to minimize $S_L$. For example, the conjugate gradient method described in the Non-Patent Document 6 may be used for the computation.

Alternatively, the consolidating parameters may be fixed and only p, q, r may be computationally determined. Still alternatively, p, q, r may be fixed and only the consolidating parameters may be computationally determined.

Figure 5:
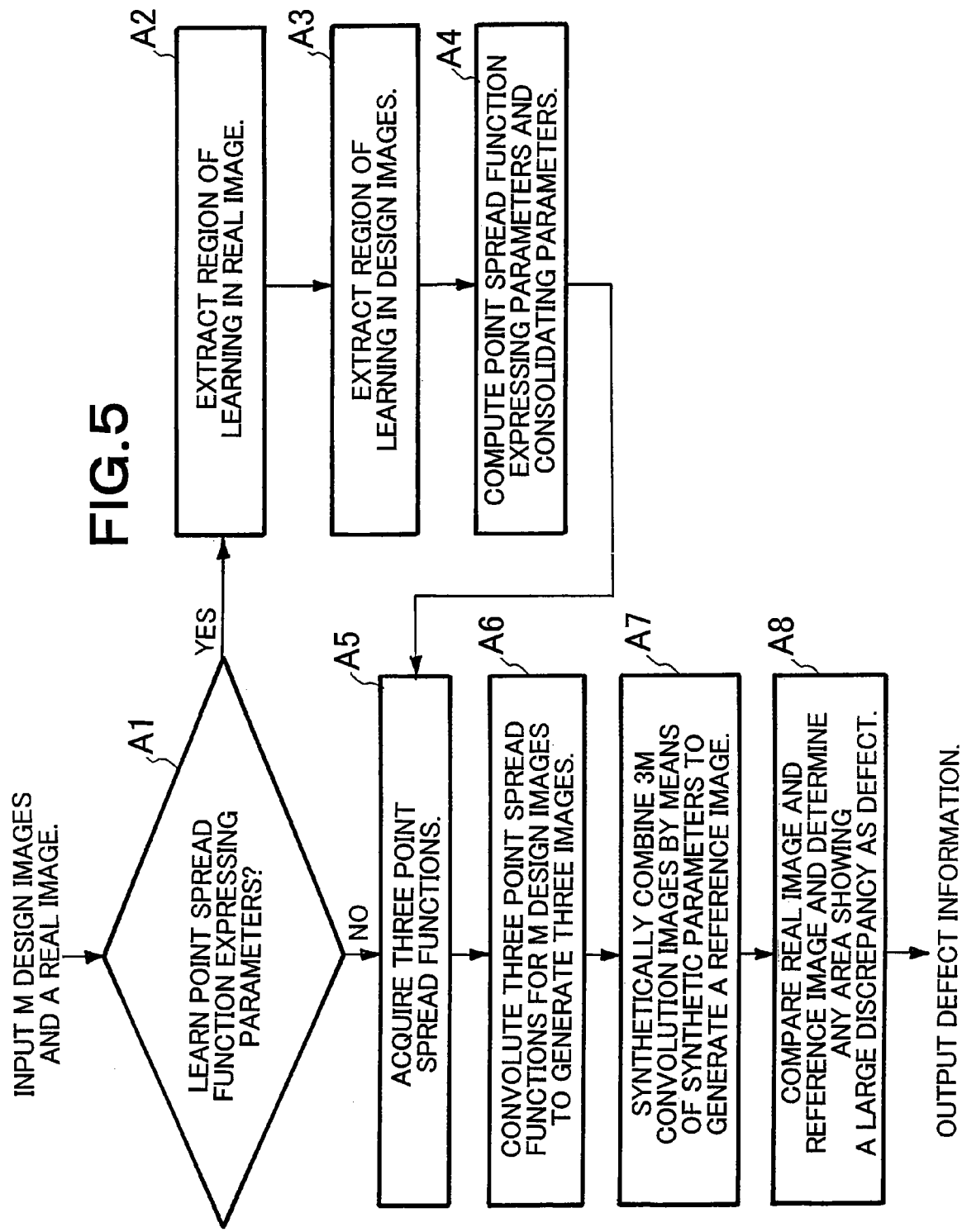
FIG. 5 is a flowchart of the operation of the embodiment of the present invention in the first aspect of thereof.

Now, the operation of the embodiment of the present invention will be described in detail by referring to FIGS. 4 and 5.

At the input apparatus 1, a real image is input from the real image input means 11, while M design images are input from the design image input means 12.

Then, it is determined if the point spread function expressing parameters that are necessary for preparing a reference image in advance are to be learnt or not when checking defects by means of the images input at the input apparatus 1 (Step A1). For example, if the parameters are to be learnt each time of inspection of a mask so as to accommodate the change of the optical system with time, the answer to the question in Step A1 is always yes.

If the user thinks that the time elapsed from the last defect checking to this time defect checking is sufficiently short if compared with the change of the optical system with time, the answer to the question in Step A1 may be no.

Alternatively, the system may be configured in such a way that no is compulsorily answered to the question of Step A1 without waiting for the user's answer when the elapsed time is short of a predetermined threshold value.

If yes is the answer to the question in Step A1, the real image input from the real image input means 11 is supplied to the partial real image extraction means 21. The partial real image extraction means 21 defines a region to be used for learning out of the real image (Step A2).

With a technique of defining a region of learning, the user may define an area for learning.

Alternatively, a region may be defined randomly. Still alternatively, all the image may be defined as a region of leaning.

This is because, if the image has a defect in part thereof, the area of the defect is very limited and the defect will not influence significantly.

However, it is a good technique to define a region of learning where many corners of a pattern to be described for a mask are contained.

This is because many corners are contained in a pattern when the pattern is a complex one. Then, it is possible to do learning by using a pattern that has many variations.

It is also a good technique to define edges running in four directions as shown in FIG. 8 along with other region of learning.

This is because the learning can result in excessive adaptation to high frequency components when only complex patterns are learnt.

Then, the M design images input from the design image input means 12 are supplied to the partial design image extraction means 22. The partial design image extraction means 22 defines the partial regions in the design images that correspond to the region of learning as defined by the partial real image extraction means 21 (Step A3).

The real image partial image obtained by the partial real image extraction means 21 and the design image partial images obtained by the partial design image extraction means 22 are supplied to the point spread function expressing parameter computation means 23.

The point spread function expressing parameter computation means 23 computationally determines the point spread function expressing parameters, using the partial images, the point spread function structuring parameters stored in the point spread function structuring parameter memory section 41 and the consolidating parameters stored in the consolidating parameter memory section 43 and stores the obtained results in the point spread function expressing parameter memory section 42 (Step A4).

When no is selected in Step A1 or yes is selected in Step A1 and a leaning is done in the processing operations down to Step A4, a defect checking operation is started at the data processing apparatus 3 on the images input from the input apparatus 1. Firstly, the design images input from the design image input means 12 are supplied to the plurality of convolution images generation means 32.

The plurality of convolution images generation means 32 firstly prepares three point spread functions from the parameters stored in the point spread function structuring parameter memory section 41 and the point spread function expressing parameter memory section 42 (Step A5) and then performs convolutional operations between M design images and the three point spread functions to generate 3M images (Step A6).

The 3M images generated by the plurality of convolution images generation means 31 are then supplied to the reference image generation means 32. The reference image generation means 32 prepares a reference image from the 3M images and the consolidating parameters stored in the consolidating parameters memory section 43 (Step A7).

The reference image prepared by the reference image generation means 32 is supplied to the image comparison means 33. The image comparison means 33 compares the real image input from the real image input means 11 and the reference image supplied from the reference image generation means 32 and determines any region showing a large discrepancy as defect (Step A8).

In this embodiment, a point spread function is expressed by means of a small number of parameters so as to estimate parameters by learning before an inspection. Therefore, it is possible to reduce both error factors of the change of the optical system with time and those not assumed for the model.

Now, an embodiment of the present invention in the second aspect will be described in detail by referring to the related drawings.

Figure 9:
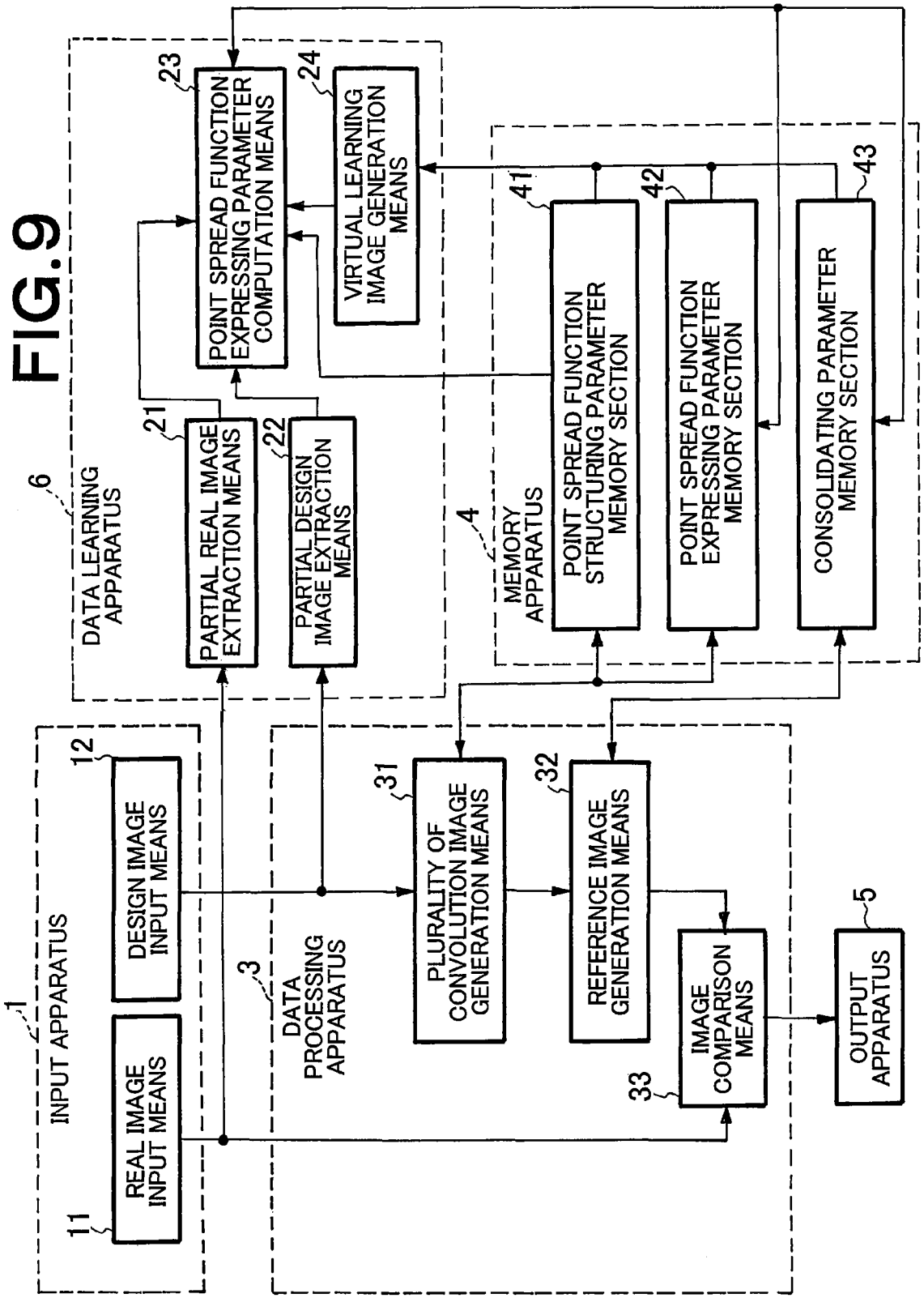
FIG. 9 is a schematic block diagram of an embodiment of the present invention in the second aspect thereof.

Referring to FIG. 9, the embodiment of the present invention in the second aspect thereof differs from the first embodiment in that the data learning apparatus 6 comprises a virtual leaning image generation means 24 in addition to the components of the data learning apparatus 2 of the first embodiment and the point spread function expressing parameter computation means 23 is specified differently relative to that of the first embodiment shown in FIG. 4.

The virtual leaning image generation means 24 prepares virtual design images apart form the design images obtained by the partial design image extraction means 22 and prepares a reference image by means of functions equivalent to those of the plurality of convolution image generation means 31 and the reference image generation means 32, using the point spread function structuring parameters, the point spread function expressing parameters and the consolidating parameters already stored in the memory apparatus 4, to provide it to the point spread function expressing parameter computation means 23 as virtual real image. The design images that the virtual learning image generation means 24 prepares may typically be step edge images running in various directions. Line patterns having various different widths may be prepared instead of step edge images. It will be better to selectively prepare line patterns having widths and directions that are not found in the design images obtained by the partial design image extraction means 22. Rectangular patterns of various different sizes may be prepared in addition to line pattern.

The point spread function expressing parameter computation means 23 computationally determines point spread function expressing parameters, using the real image obtained by the partial real image extraction means 21, the design images obtained by the partial design image extraction means 22 and the virtual real image and the design images obtained by the virtual learning image generation means 24.

Figure 10:
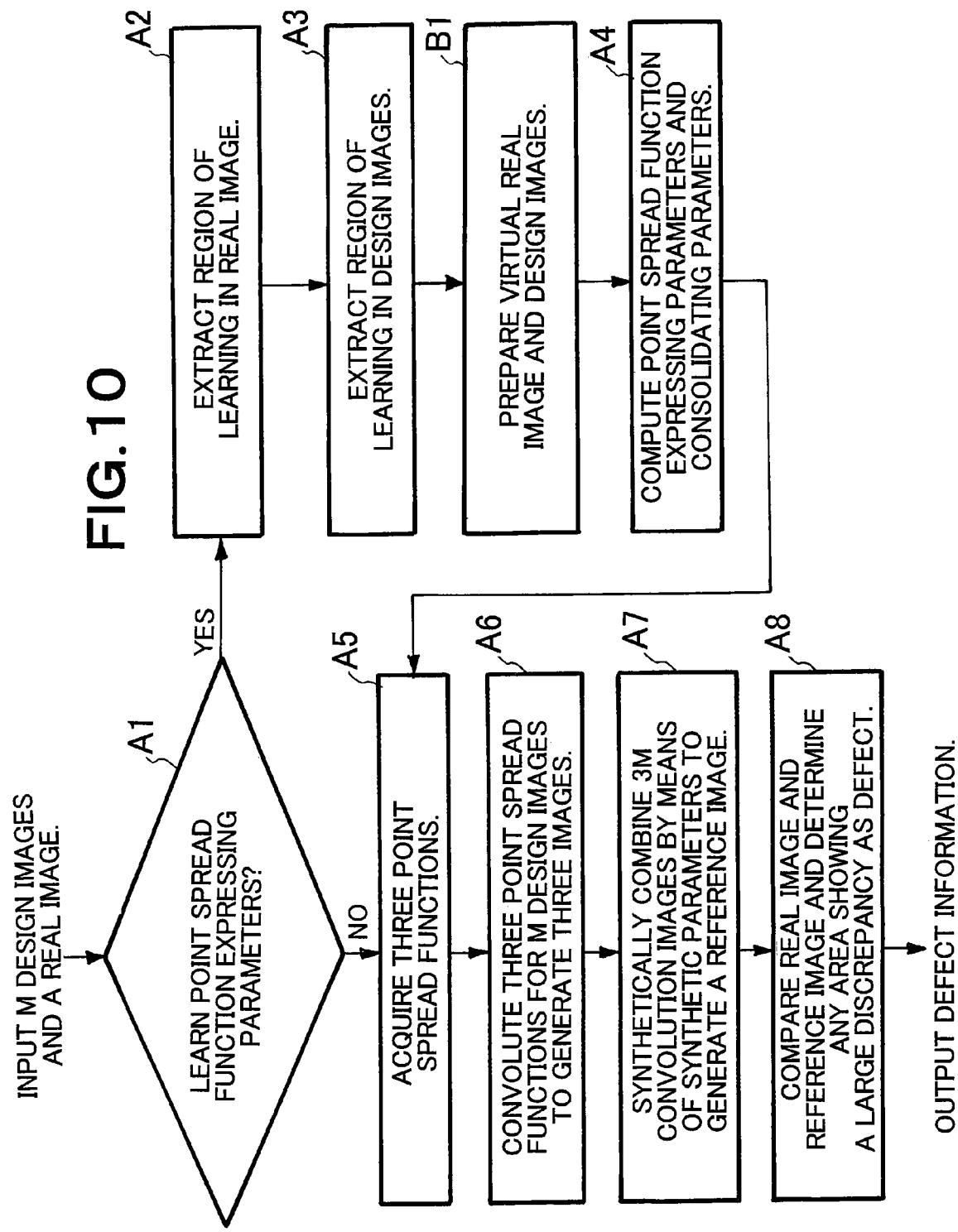
FIG. 10 is a flowchart of the operation of the embodiment of the present invention in the second aspect thereof.

Now, the overall operation of this embodiment will be described by referring to FIG. 9 and the flowchart of FIG. 10.

Since the operations in Steps A1, A2, A3, A5, A6, A7 and A8 are the same as those of the above embodiment of the present invention, they will not be described here repeatedly.

In this embodiment, the virtual leaning image generation means 24 generates virtual design images and a virtual real image after Step A3 (Step B1). The virtual design images and the virtual real image generated in Step B1 are provided to the point spread function expressing parameter computation means 23 with the real image and the reference image generated in Steps A2 and A3 respectively.

The point spread function expressing parameter computation means 23 computationally determines point spread function expressing parameters, using the real image obtained by the partial real image extraction means 21, the design images obtained by the partial design image extraction means 22 and the virtual leaning image generation means 24 (Step A4).

Now, the advantages of this embodiment of the invention will be described below.

This embodiment of the present invention can increase learning data even when the types of patterns of the region of learning by supplementing virtual images. Then, as a result, it is possible to maintain the level of precision relative to unlearnt patterns.

Now, an embodiment of the present invention in the third aspect of the invention will be described in detail by referring to the related drawings.

Figure 11:
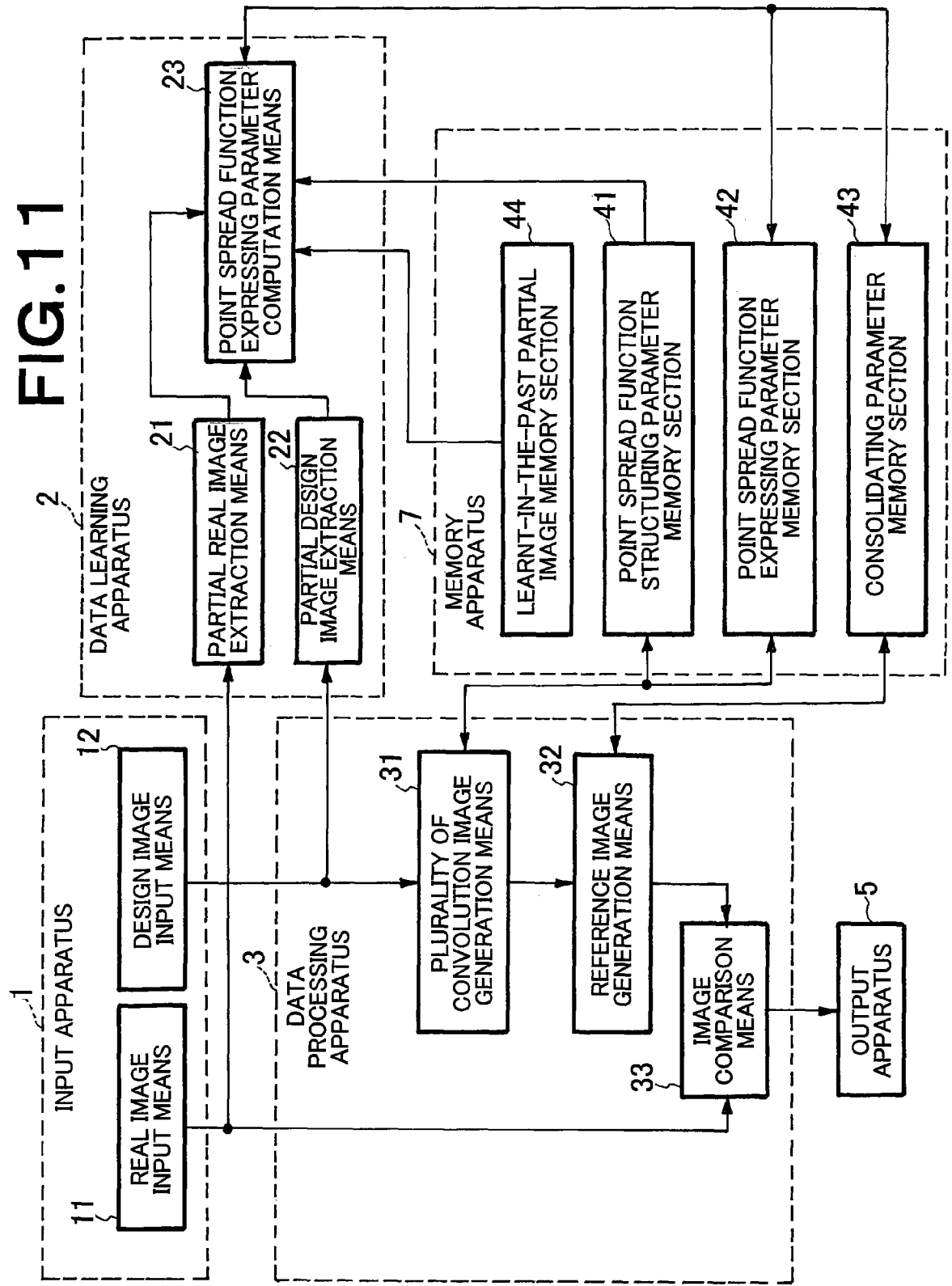
FIG. 11 is a schematic block diagram of an embodiment of the present invention in the third aspect thereof.

Referring to FIG. 11, the embodiment of the present invention in the third aspect thereof differs from the first embodiment in that the memory apparatus 3 of this embodiment comprises a learnt-in-the-past partial image memory section 44 in addition to the components of the memory apparatus 3 of the first embodiment and the point spread function expressing parameter computation means 23 is specified differently relative to that of the first embodiment shown in FIG. 4.

The learnt-in-the-past partial image memory section 44 stores the partial real images used by the data learning apparatus in the past and the corresponding partial reference images and provides them to the point spread function expressing parameter computation means 23. The learnt-in-the-past partial image memory section 44 may provide all the real images and all the reference images it stores. It is better for the learnt-in-the-past partial image memory section 44 to provide only the line patterns it sores among the line patterns showing widths and directions that are not found in the design images obtained by the partial design image extraction means 22.

The point spread function expressing parameter computation means 23 computationally determines the point spread function expressing parameters, using the real image obtained by the partial real image extraction means 21, the design images obtained by the partial design image extraction means 22 and the real images and the design images used in the past for learning and given from the learnt-in-the-past partial image memory section 44.

Figure 12:
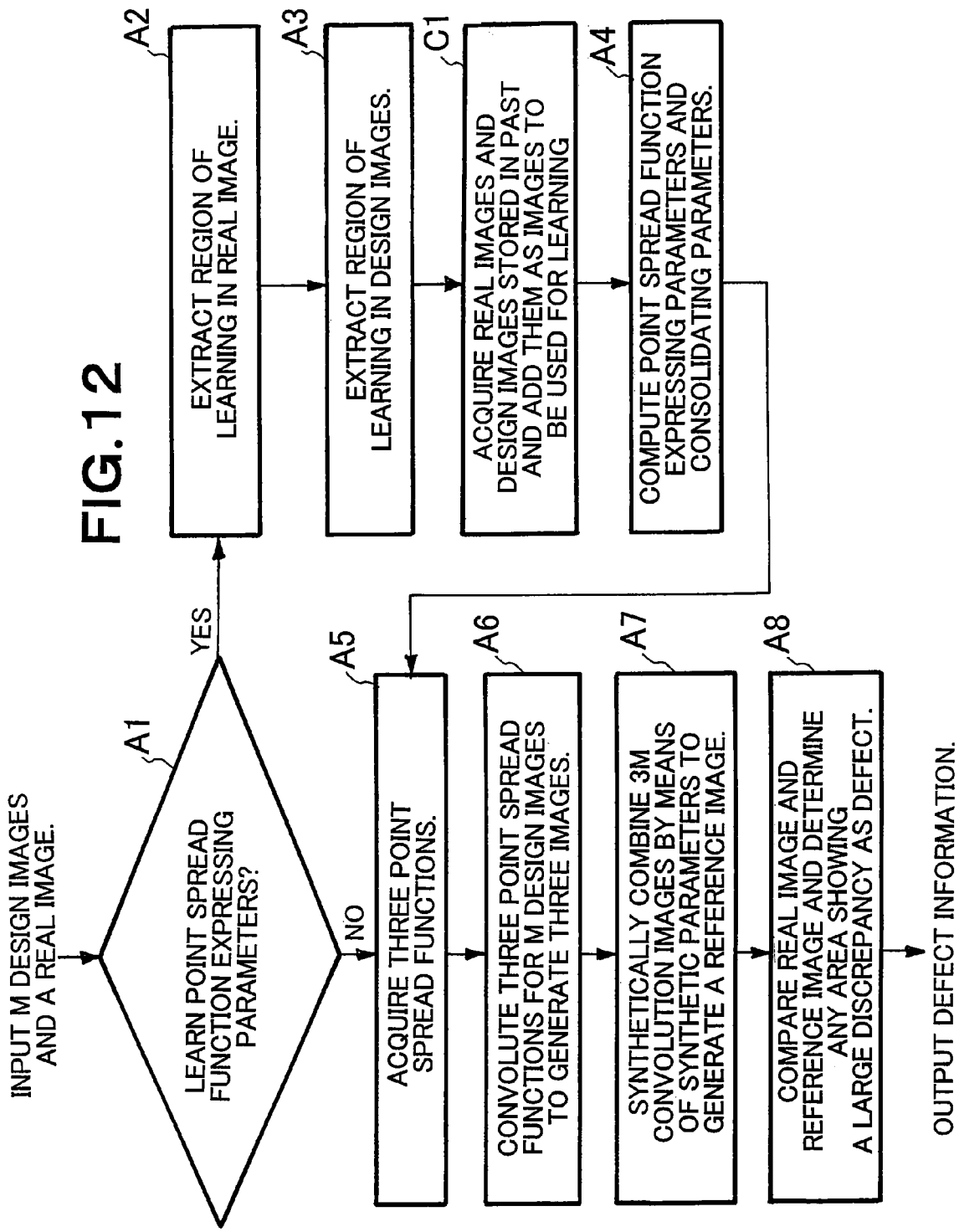
FIG. 12 is a flowchart of the operation of the embodiment of the present invention in the third aspect thereof.

Now, the overall operation of this embodiment will be described by referring to FIG. 11 and the flowchart of FIG. 12.

Since the operations in Steps A1, A2, A3, A5, A6, A7 and A8 are the same as those of the above embodiment of the present invention, they will not be described here repeatedly.

After Step A3, this embodiment takes out the real images and the design images used in the past for leaning and stored in the learnt-in-the-past partial image memory section 44 (Step C1) in addition to the real image and the reference image obtained in Step A3 and provides all the images to the point spread function expressing parameter computation means 23.

The point spread function expressing parameter computation means 23 computationally determines the point spread function expressing parameters, using the real image obtained by the partial real image extraction means 21, the design images obtained by the partial design image extraction means 22 and the real images and the design images used in the past for leaning and given from the learnt-in-the-past partial image memory section 44 (Step A4).

Now, the advantages of this embodiment of the invention will be described below.

This embodiment of the present invention can increase learning data even when the types of patterns of the region of learning by supplementing the images used in the previous learning. Then, as a result, it is possible to maintain the level of precision relative to unlearnt patterns.

Now, an embodiment of the present invention in the fourth aspect of the invention will be described in detail by referring to the related drawings.

Figure 13:
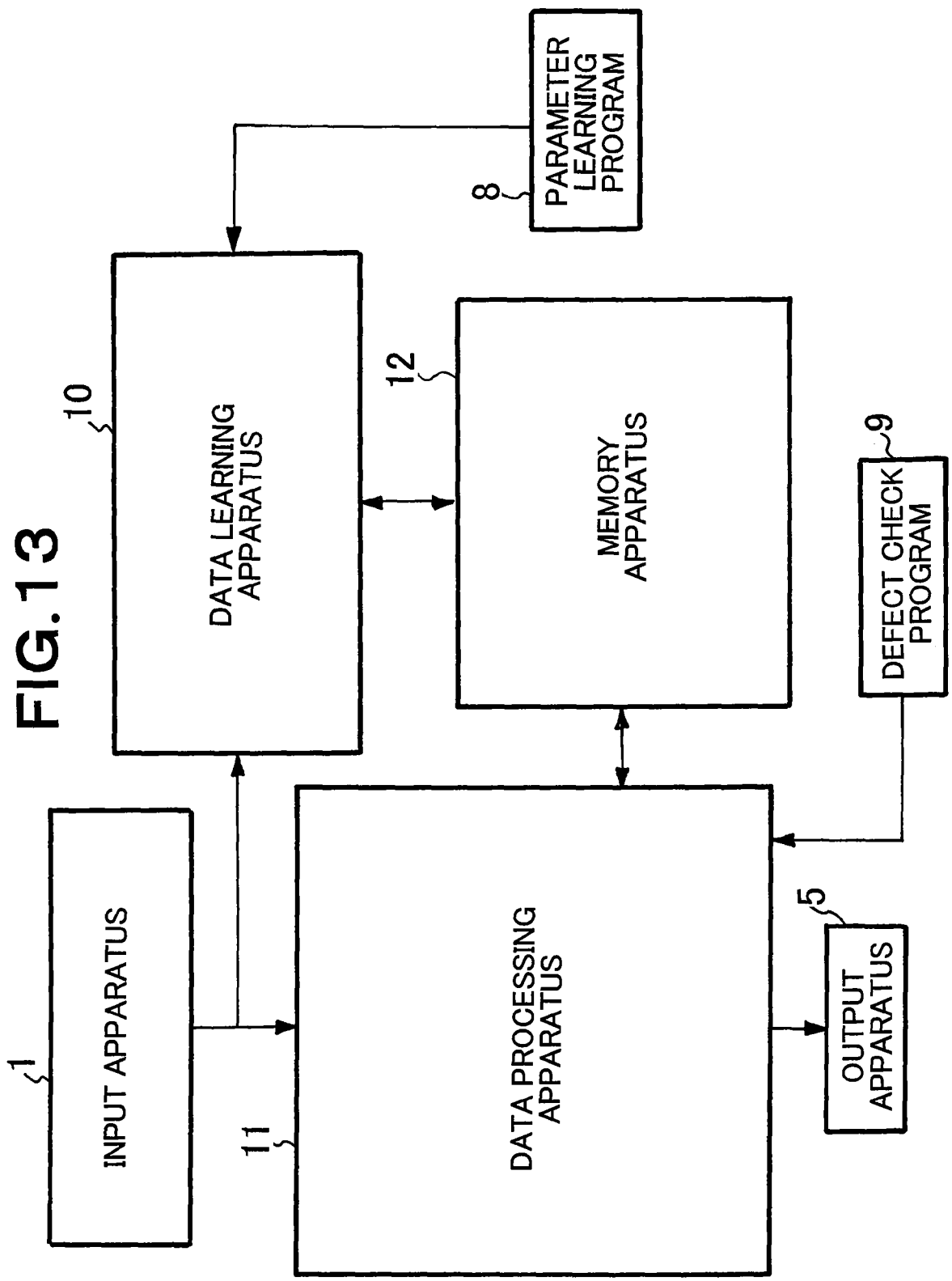
FIG. 13 is a schematic block diagram of an embodiment of the present invention in the fourth aspect thereof.

Referring to FIG. 13, the embodiment of the present invention in the fourth aspect thereof comprises an input apparatus, a data leaning apparatus, a data processing apparatus, a memory apparatus and an output apparatus like the embodiments in the first, second and third aspects of the invention.

The parameter leaning program 8 is read into the data learning apparatus 10 to control the operation of the data learning apparatus 10 and execute the process same as those of the data learning apparatus 2 and 6 of the first, second and third embodiments.

The defect check program 9 is read into the data processing apparatus 9 to control the operation of the data processing apparatus 11 and execute the process same as those of the data processing apparatus 3 of the first, second and third embodiments.

EXAMPLE 1

Now, the embodiment of the present invention will be described further by way of a specific example with reference to FIG. 4. In this example, both the data leaning apparatus and the data processing apparatus utilize the central processing unit of a personal computer. Additionally, a magnetic disk apparatus is utilized as data memory apparatus. Assume here that a half tone mask as shown in FIG. 2 is input for inspection and the computation formula (8) is applied to generate a reference image. A half tone mask can be regarded as transmittance image showing two different transmittances and, when the formula (8) is used, M=1 is assumed because the value of M is decremented by 1 as shown at the right side of the formula (8).

The magnetic disk apparatus stores the consolidating parameters A, B, C, $a_1$, $b_1$, $c_1$, the point spread function structuring parameters $w_1(x, y)$, $w_2(x, y)$ (x=−1, 0, +1; y=−1, 0, +1) as shown in FIG. 14 and the point spread function parameter expressing parameters $p_1$, $p_2$, $q_1$, $q_2$, $r_1$, $r_2$. The point spread function expressing parameters $p_1$, $p_2$ are parameters for expressing the first point spread function $h_p(x, y)$, the point spread function expressing parameters $q_1$, $q_2$ are parameters for expressing the second point spread function $h_q(x, y)$ and $r_1$, $r_2$ are parameters for expressing the third point spread function $h_r(x, y)$. They can be computationally determined by means of the respective point spread function structuring parameters and product-sum operations as expressed by the formula below in a manner as illustrated in FIG. 15.

[formula 33]

$$h_p(x, y) = p_1 w_1(x, y) + p_2 w_2(x, y) \quad (10)$$

$$h_q(x, y) = q_1 w_1(x, y) + q_2 w_2(x, y) \quad (11)$$

$$h_r(x, y) = r_1 w_1(x, y) + r_2 w_2(x, y) \quad (12)$$

This time, the formula (5) is used to computationally determine a reference image. Since M=1, the formula (5) is reduced to the formula show below.

[formula 34]

$$G(x, y) = [\{a_1(f_1 * h_p) - b_1(f_1 * h_q)\} + A]^2 + [b_1(f_1 * h_p) + a_1(f_1 * h_q) + B]^2 + c_1(f_1 * h_r) + C \quad (13)$$

Or, by using the formulas (10), (11) and (12) as substitutes, the formula for determining G(x, y) is can also be expressed by the formula below.

[formula 35]

$$G(x, y) = [\{a_1(p_1 T_1 + p_2 T_2) - b_1(q_1 T_1 + q_2 T_2)\} + A]^2 + [b_1(p_1 T_1 + p_2 T_2) + a_1(q_1 T_1 + q_2 T_2) + B]^2 + c_1(r_1 T_1 + r_2 T_2) + C \quad (14)$$

where $T_1$ and $T_2$ are quantities that can be computationally determined by the formulas shown below.

[formula 36]

$$T_1 = f_1 * w_1 = \sum_{i=-1}^{1} \sum_{j=-1}^{1} f_1(x-i, y-j) w_1(i, j)$$

$$T_2 = f_1 * w_2 = \sum_{i=-1}^{1} \sum_{j=-1}^{1} f_1(x-i, y-j) w_2(i, j)$$

In this example, the formula (13), or the formula (14) that is equivalent to the formula (13) is utilized to computationally determine the reference image.

Figure 16:
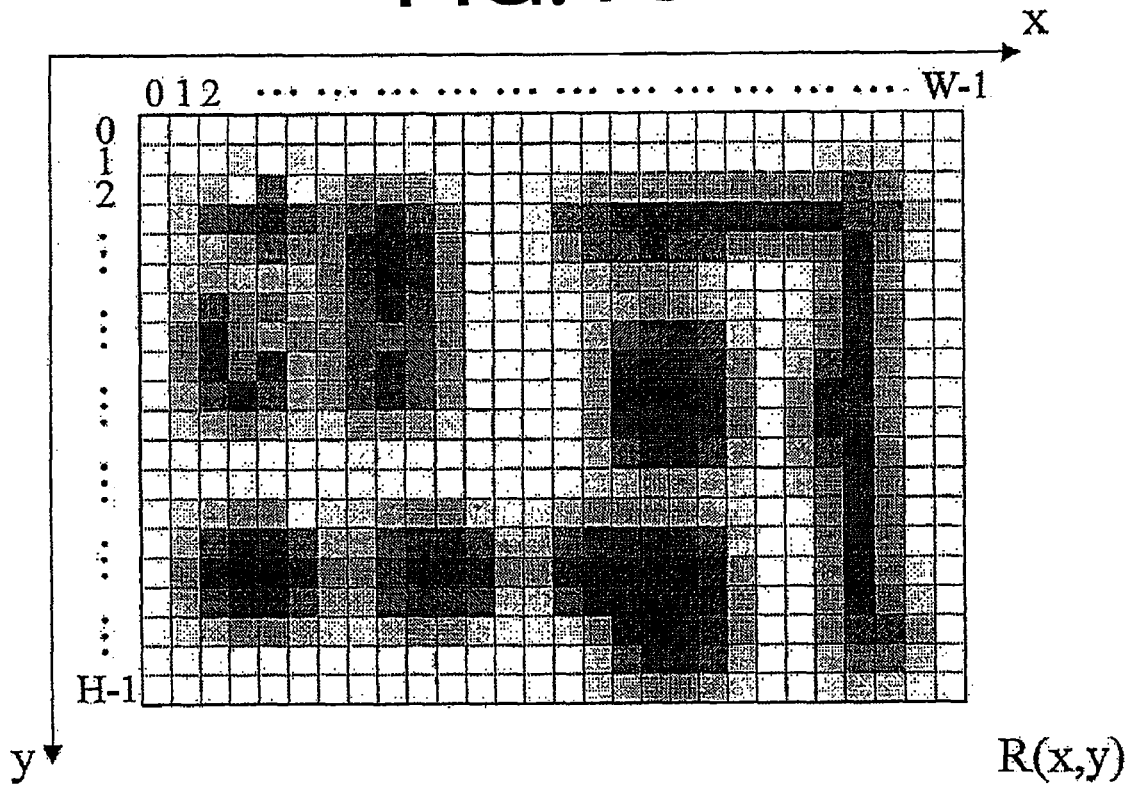
FIG. 16 is a specific illustration of an exemplary real image.
Figure 17:
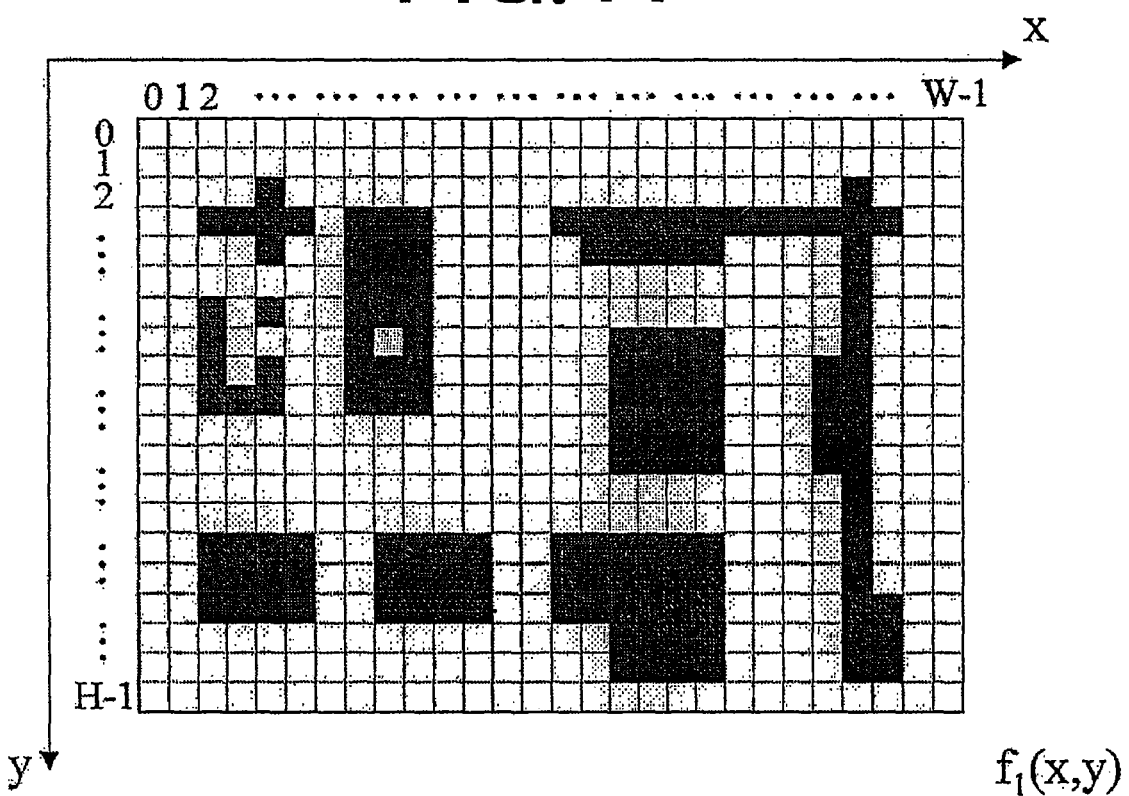
FIG. 17 is a schematic illustration of (the first sheet of) an exemplary design image.
Figure 18:
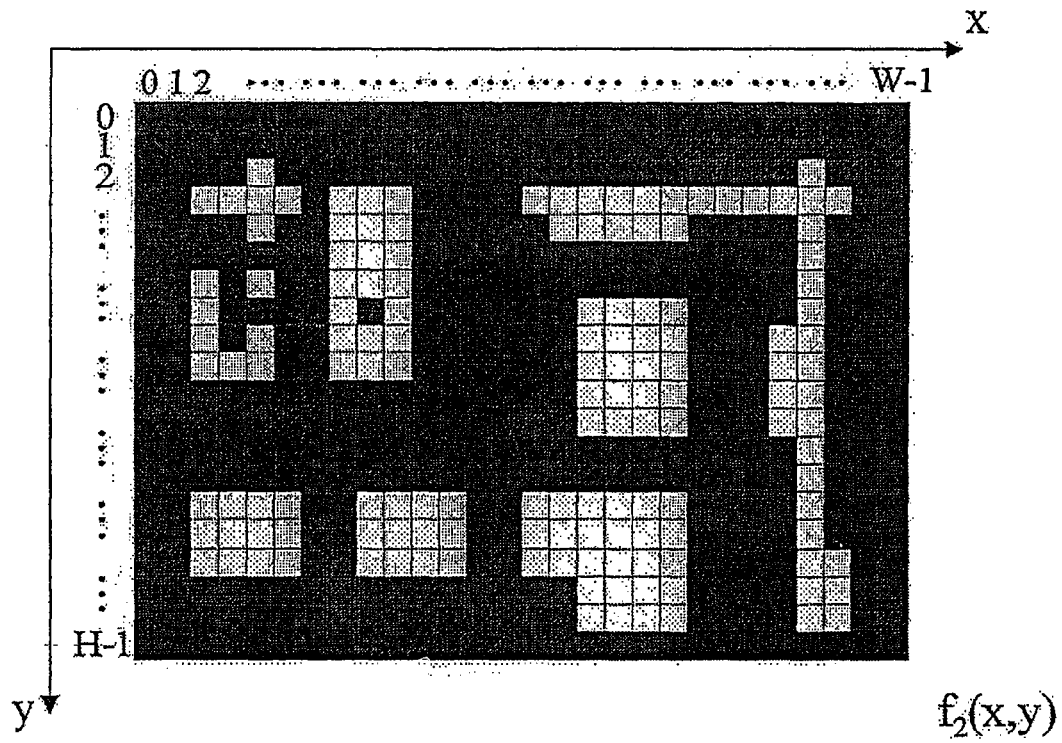
FIG. 18 is a schematic illustration of (the second sheet) of an exemplary design image.

Firstly, assume that a half tone mask real image R(x, y) (x=0, ..., W−1, y=0, ..., H−1) having a width of W in the x-direction and a width of H in the y-direction as shown in FIG. 16 and half tone mask design images $f_1(x, y)$, $f_2(x, y)$ (x=0, ..., W−1, y=0, ..., H−1) as shown in FIGS. 17 and 18 are input. As seen from the formula (10) or (11), it is sufficient to use only the design image $f_1(x, y)$ out of the two design images.

Figure 19:
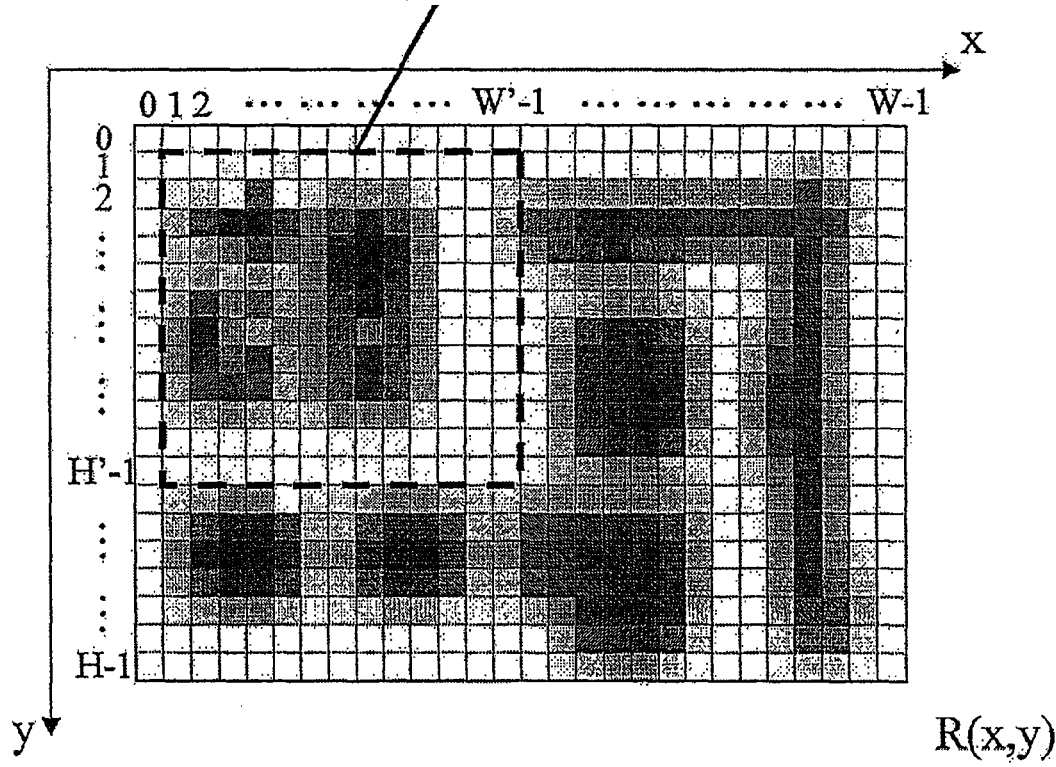
FIG. 19 is a schematic illustration of a specific example of a region for learning defined in a real image.
Figure 20:
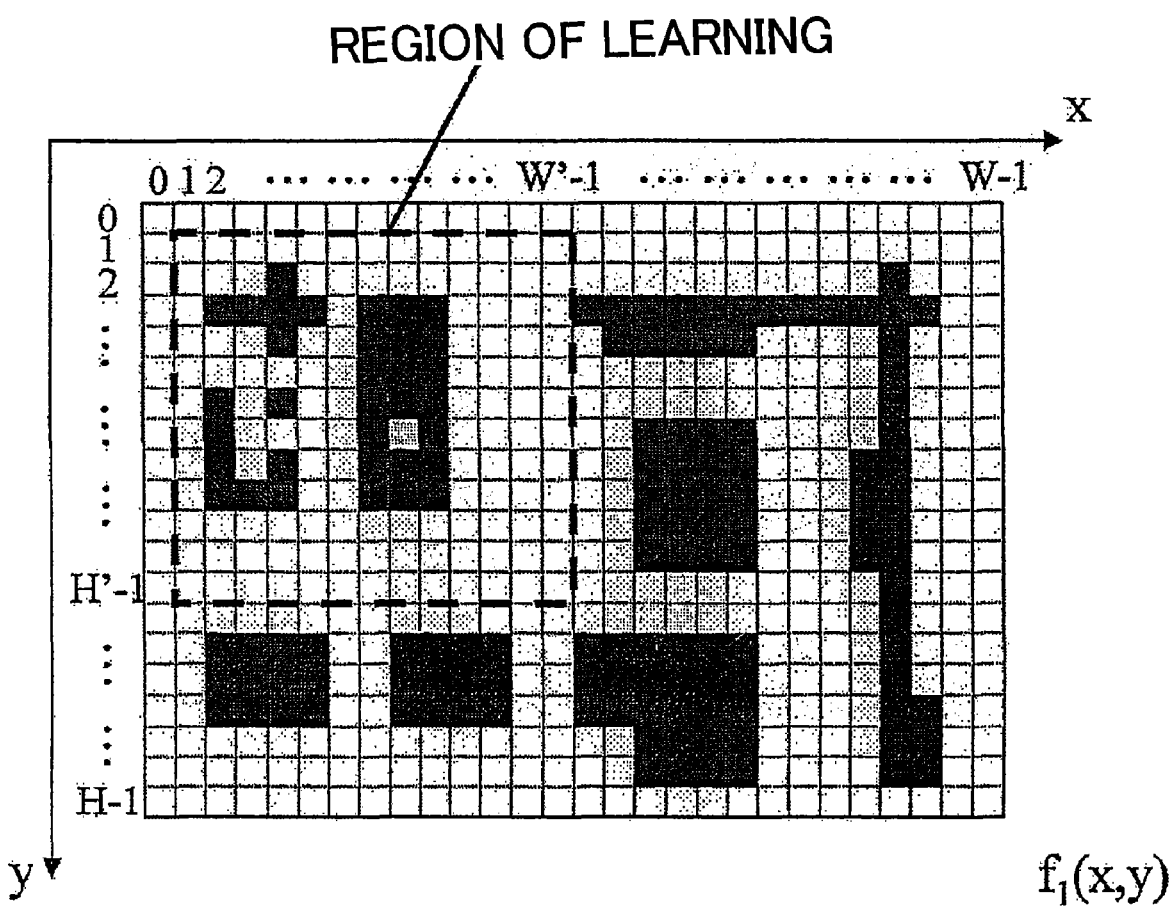
FIG. 20 is a schematic illustration of a specific example of a region for learning defined in a design image.

The parameters are updated by learning on the basis of the real image R(x, y) and the design image $f_1(x, y)$ that are input (Yes to the question in Step A1). Then, the partial image to be used for the learning is defined. Here, the region to be used for the learning is defined by 0<x<W' and 0<y<H' and also as L. The partial real image to be used for the learning is the rectangular region R(x, y) ((x, y)□L) surrounded by dotted lines in FIG. 19 and the partial reference image to be used for the learning is the rectangular region $f_1(x, y)$((x, y)∈L) surrounded by dotted lines in FIG. 20 (Steps A2, A3).

Then, the point spread function expressing parameters $p_1$, $p_2$, $q_1$, $q_2$, $r_1$, $r_2$ and the structure parameters $a_1$, $b_1$, $c_1$, A, B, C that minimize the value of $S_L$ of the formula (9), which is computed by reading out the point spread function structuring parameters $w_1(x, y)$, $w_2(x, y)$ stored in the magnetic memory apparatus and using the formula (11), are computationally determined by means of the conjugate gradient method.

Then, the values of $p_1$, $p_2$, $q_1$, $q_2$, $r_1$, $r_2$, $a_1$, $b_1$, $c_1$, A, B, C stored in the magnetic memory apparatus are replaced by the above described values that are computationally determined by means of the conjugate gradient method. (Step A4).

Then, the defect check process is executed on the input images. The central processing unit reads in the point spread function expressing parameters $p_1$, $p_2$, $q_1$, $q_2$, $r_1$, $r_2$ and the point spread function structuring parameters $w_1(x, y)$, $w_2(x, y)$ stored in the magnetic memory apparatus and determines the three point spread functions $h_p$, $h_q$ and $h_r$ by means of the formulas (10), (11) and (12).

Then, $f_1$ and the three point spread functions $h_p$, $h_q$, $h_r$ are convoluted (Step A6) and the structuring parameters $a_1$, $b_1$, $c_1$, A, B, C stored in the magnetic memory apparatus are read in. Then, the reference image G(x, y) is prepared by means of the formula (10) (Step A7).

After preparing the reference image G(x, y), the absolute value of the difference between the real image R(x, y) and the reference value G(x, y) is checked and any point (x, y) where the relationship of

[formula 37]

$$|R(x, y) - G(x, y)| > T$$

holds true is determined to be a defect, using a predetermined value T (Step A8).

INDUSTRIAL APPLICABILITY

The present invention is applicable to mask defect inspections necessary in the process of manufacturing semiconductors that are to be made by comparing a real image obtained by scanning a processed pattern and a reference image generated by using design images corresponding to the scanned and processed pattern.

The invention claimed is:

1. A reference image generation apparatus, comprising:
a point spread function estimating section for estimating a function expressing a coherent optical effect and an incoherent optical effect from an observation image and design information;
a convolution image generating section for generating a convolution image by convoluting the point spread function relative to the design information; and
a reference image generating section for generating a reference image from the convolution image obtained by the convolution image generating section,
wherein the function comprises a plurality of point spread functions, where each point spread function in the plurality expresses a coherent optical effect and an incoherent optical effect, and the function estimates variables of the plurality of point spread functions as uncorrelated variables.

2. The apparatus according to claim 1, characterized in that the point spread function is expressed by not more than a predetermined number of parameters.

3. The apparatus according to claim 1, characterized in that the point spread function is expressed by a Gaussian functions.

4. The apparatus according to claim 1, characterized in that the point function is expressed by a product-sum operation.

5. The apparatus according to claim 1, characterized in that the point spread function is isotropic.

6. The apparatus according to claim 1, characterized in that the point spread function shows a profile admitting distortions.

7. The apparatus according to claim 1, characterized in that the observation image and the design information include not only information on the pattern being currently inspected but also virtual design images and the reference image generated from a convolution image generated by convoluting the virtual design images, using the point spread functions obtained in the past, as virtual observation images.

8. The apparatus according to claim 1, characterized in that the observation image and the design information include not only those relating to the pattern being currently inspected but also the patterns inspected in the past.

9. A pattern inspection apparatus characterized by comprising: a reference image generating apparatus according to claim 1; and an image comparing section for comparing the observation image and the reference image.

10. A reference image generation apparatus, comprising:
a point spread function estimating section for estimating a point spread function from an observation image and design information;
a convolution image generating section for generating a plurality of convolution images by convoluting the point spread function relative to the design information; and
a reference image generating section for generating a reference image from the plurality of convolution images obtained by the convolution image generating section;
wherein the point spread function estimating section expresses the point spread function by means of point spread function structuring parameters and point spread function expressing parameters.

11. The apparatus according to claim 10, characterized in that the reference image generating section estimates consolidating parameters for the plurality of convolution images.

12. The apparatus according to claim 10, characterized in that the point spread function estimating section further inputs the point spread function structuring parameters to estimate the consolidating parameters.

13. The apparatus according to claim 10, characterized in that the user specifies the point spread function structuring parameters.

14. The apparatus according to claim 10, characterized in that past parameters are also used as the point spread function structuring parameters.

15. The apparatus according to claim 10, characterized in that the observation image and the design information include not only information on a pattern being currently inspected, but also virtual design images and the reference image generated from a convolution image generated by convoluting the virtual design images, using the point spread functions obtained in the past, as virtual observation images.

16. The apparatus according to claim 10, characterized in that the observation image and the design information include not only those relating to a pattern being currently inspected, but also past patterns inspected.

17. The apparatus according to claim 10, characterized in that the point spread function estimating section further inputs point spread function structuring parameters to estimate point spread function expressing parameters.

18. A computer readable recording medium recording a pattern inspection program for causing a computer to execute a pattern inspection method, the method comprising:
a point spread function estimating step of estimating a function expressing a coherent optical effect and an incoherent optical effect from an observation image and design information;
a convolution image generating step of generating a convolution image by convoluting the function relative to the design information;
a reference image generating step of generating a reference image from the convolution image obtained in the convolution image generating step; and
an image comparing step of comparing the observation image and the reference image,
wherein the function comprises a plurality of point spread functions, where each point spread function in the plurality expresses a coherent optical effect and an incoherent optical effect, and the function estimates variables of the plurality of spread functions as uncorrelated variables.

19. A computer readable recording medium recording a reference image generation program for causing a computer to execute a reference image generation method comprising:

a point spread function estimating step of estimating a function expressing a coherent optical effect and an incoherent optical effect from an observation image and design information;

a convolution image generating step of generating a convolution image by convoluting the function relative to the design information; and a reference image generating step of generating a reference image from the convolution image obtained in the convolution image generating step, wherein the function comprises a plurality of point spread functions, where each point spread function in the plurality expresses a coherent optical effect and an incoherent optical effect, and the function estimates variables of the plurality of point spread functions as uncorrelated variables.

* * * * *